US009714279B2

(12) United States Patent
Fernandez et al.

(10) Patent No.: US 9,714,279 B2
(45) Date of Patent: Jul. 25, 2017

(54) HIV VPR-SPECIFIC T-CELL RECEPTORS

(71) Applicant: Altor BioScience Corporation, Miramar, FL (US)

(72) Inventors: Marilyn Fernandez, Surfside, FL (US); Bai Liu, Cooper City, FL (US); Warren D. Marcus, Miramar, FL (US); Hing C. Wong, Weston, FL (US)

(73) Assignee: Altor Bioscience Corporation, Miramar, FL (US)

( * ) Notice: Subject to any disclaimer, the term of this patent is extended or adjusted under 35 U.S.C. 154(b) by 140 days.

(21) Appl. No.: 14/560,314

(22) Filed: Dec. 4, 2014

(65) Prior Publication Data

US 2015/0087059 A1    Mar. 26, 2015

Related U.S. Application Data

(62) Division of application No. 12/731,485, filed on Mar. 25, 2010, now Pat. No. 8,933,198.

(60) Provisional application No. 61/163,421, filed on Mar. 25, 2009.

(51) Int. Cl.
*C07K 14/725* (2006.01)
*C07K 14/705* (2006.01)
*G01N 33/569* (2006.01)

(52) U.S. Cl.
CPC ...... *C07K 14/70503* (2013.01); *C07K 14/705* (2013.01); *C07K 14/7051* (2013.01); *G01N 33/56988* (2013.01)

(58) Field of Classification Search
CPC .............. C07K 14/70503; C07K 14/7051
See application file for complete search history.

(56) References Cited

U.S. PATENT DOCUMENTS

2004/0253632 A1    12/2004   Rhode et al.
2008/0015139 A1    1/2008    Lichterfeld et al.

FOREIGN PATENT DOCUMENTS

WO    2006/103429 A2    10/2006

OTHER PUBLICATIONS

Goyarts, E. C., et al., 1998, Point mutations in the beta chain of CDR3 can alter the T cell receptor recognition pattern on an MHC class I/peptide complex over a braod interface area, Mol. Immunol. 35:593-607.*
Klein, M. H., et al., 1987, Diversity and structure of human T-cell receptor alpha-chain variable region genes, Proc. Natl. Acad. Sci. USA 84:6884-6888.*
Arden, B., et al., 1995, Human T-cell receptor variable gene segment families, Immunogenetics 42:455-500.*
Yu, X. G., et al., 2007, Random T-cell receptor recruitment in human immunodeficiency virus type 1 (HIV-1)-specific CD8+ T cells from genetically identical twins infected with the same HIV-1 strain, J. Virol. 81(22):12666-12669.*
Altfeld, Marcus A., et al., "Identification of Novel HLA-A2-Restricted Human Immunodeficiency Virus Type 1-Specific Cytotxic T-Lymphocyte Epitopes Predicted by the HLA-A2 Supertype Peptide-Binding Motif", Journal of Virology, Feb. 2001, 75(3):1301-1311.
Altfeld, Marcus, et al., "The Majority of Currently Circulating Human Immunodeficiency Virus Type 1Clade B Viruses Fail to Prime Cytotoxic T-Lymphocyte Responses against an Otherwise Immunodominant HLA-A2-Restricted Epitope: Implications for Vaccine Design", Journal of Virology, Apr. 2005, 79(8):5000-5005.
Altfeld, Marcus et al., Vpr is preferentially targeted by CTL during HIV-1 infection, J. Immunology, 2001, 167:2743-2752.
Goyarts, E.C., et al., 1998, Point mutations in the beta chain of CDR3 can alter the T cell receptor recognition pattern on an MHC class I/peptide complex over a broad interface area, Mol. Immunol. 35:593-607.
Klein, M.H. et al., Oct. 1987, Diversity and structure of human T-cell receptor alpha-chain variable region genes, Proc. Natl. Acad. Sci. USA, 84:6884-6888.
Srinivasan, Alagarsamy, et al., "A comprehensice analysis of the naturally occurring polymorphisms in HIV-1 Vpr: Potential impact on CTL epitopes", Virology Journal, Aug. 2008, 5(1):1-17.
Varela-Rohena, A., et al., Dec. 2008, Control of HIV-1 immune escape by CD8 T cells expressing enhanced T-cell receptor, Nat. Med. 14(12):1390-1395.
Yu, X. G. et al., Nov. 2007, Random T-cell receptor recruitment in human immunodeficiency virus type 1(HIV-1) specific CD8+ T cells from genetically identical twins infected with the same strain, J. Virol. 81(22):12666-12669.

* cited by examiner

*Primary Examiner* — Jeffrey Parkin
(74) *Attorney, Agent, or Firm* — Mintz Levin Cohn Ferris Glovsky and Popeo, P.C.; Peter F. Corless; Carolina E. Säve

(57) ABSTRACT

The instant invention provides TCRs having one or more amino acid substitutions that bind to the AL9 epitope of the HIV protein vpr (AIIRILQQQL).

26 Claims, 40 Drawing Sheets

Figure 1A. AL9scTCR wild type protein sequence (CDRs italicized)

```
                              -CDR1--                       --
GEDVEQSLFL SVREGDSSVI NCTYTDSSST YLYWYKQESG AGLQLLTYIF
<--------------------TCR Vα (TRAV5/TRAVJ36)------------------------------

CDR2                                            ---CDR3------
SNMDMKQDQR LTVLLNKKDK HLSLRIADTQ TGDSAIYFCA ETYQTGANNL
--------------------TCR Vα------------------------------------------------

FFGTGTRLTV IP
----TCR Vα-------->

TSGGGGSGGG ASGGGGSGGG GSSS
<-----------------Linker------------------->

-CDR1-                       --
EAGVTQFPSH SVIEKGQTVT LRCDPISGHD NLYWYRRVMG KEIKFLLHFV
<--------------------TCR Vβ (TRBV14/TRBJ2-1)------------------------------

CDR2                                            ---CDR3-
KESKQDESGM PNNRFLAERT GGTYSTLKVQ PAELEDSGVY FCASSQGVTL
--------------------TCR Vβ------------------------------------------------

LNEQFFGPGT RLTVL
--------TCR Vβ-------->

EDLNKVFPPE VAVFEPSEAE ISHTQKATLV CLATGFFPDH VELSWWVNGK
<--------------------TCR Cβ------------------------------------------------

EVHSGVSTDP QPLKEQPALN DSRYCLSSRL RVSATFWQNP RNHFRCQVQF
--------------------TCR Cβ------------------------------------------------

YGLSENDEWT QDRAKPVTQI VSAEAWGRAD (SEQ ID NO: 3)
--------------------TCR Cβ------------------------>
```

Figure 1B. AL9scTCR single mutant (Y93H) protein sequence

GEDVEQSLFL SVREGDSSVI NCTYTDSSST YLYWYKQESG AGLQLLTYIF
<--------------------TCR Vα--------------------------------------------------

SNMDMKQDQR LTVLLNKKDK HLSLRIADTQ TGDSAIYFCA ETHQTGANNL
--------------------TCR Vα------------------------------------- ^ ------------
                               Y>H mutation

FFGTGTRLTV IP
----TCR Vα-------->

TSGGGGSGGG ASGGGGSGGG GSSS
<----------------Linker------------------>

EAGVTQFPSH SVIEKGQTVT LRCDPISGHD NLYWYRRVMG KEIKFLLHFV
<--------------------TCR Vβ--------------------------------------------------

KESKQDESGM PNNRFLAERT GGTYSTLKVQ PAELEDSGVY FCASSQGVTL
--------------------TCR Vβ---------------------------------------------------

LNEQFFGPGT RLTVL
--------TCR Vβ-------->

EDLNKVFPPE VAVFEPSEAE ISHTQKATLV CLATGFFPDH VELSWWVNGK
<--------------------TCR Cβ--------------------------------------------------

EVHSGVSTDP QPLKEQPALN DSRYCLSSRL RVSATFWQNP RNHFRCQVQF
--------------------TCR Cβ---------------------------------------------------

YGLSENDEWT QDRAKPVTQI VSAEAWGRAD (SEQ ID NO: 4)
--------------------TCR Cβ------------------------>

Figure 1C. AL9scTCR double mutant (S39P, Y93H) protein sequence

GEDVEQSLFL SVREGDSSVI NCTYTDSSST YLYWYKQEPG AGLQLLTYIF
<---------------------TCR Vα-------------------------------------------^----------------------
                                                              S>P mutation SNMDMKQDQR LTVLLNKKDK HLSLRIADTQ TGDSAIYFCA ETHQTGANNL
---------------------TCR Vα-------------------------------------------- ^ ------------
                                                              Y>H mutation

FFGTGTRLTV IP
----TCR Vα-------->

TSGGGGSGGG ASGGGGSGGG GSSS
<-----------------Linker------------------->

EAGVTQFPSH SVIEKGQTVT LRCDPISGHD NLYWYRRVMG KEIKFLLHFV
<---------------------TCR Vβ-------------------------------------------

KESKQDESGM PNNRFLAERT GGTYSTLKVQ PAELEDSGVY FCASSQGVTL
---------------------TCR Vβ-------------------------------------------

LNEQFFGPGT RLTVL
--------TCR Vβ-------->

EDLNKVFPPE VAVFEPSEAE ISHTQKATLV CLATGFFPDH VELSWWVNGK
<---------------------TCR Cβ-------------------------------------------

EVHSGVSTDP QPLKEQPALN DSRYCLSSRL RVSATFWQNP RNHFRCQVQF
----------------------TCR Cβ------------------------------------------

YGLSENDEWT QDRAKPVTQI VSAEAWGRAD (SEQ ID NO: 5)
---------------------TCR Cβ------------------------>

Figure 2A. AL9scTCR wild type nucleic acid sequence (CDRs italicized)

```
GGAGAGGATGTGGAGCAGAGTCTTTTCCTGAGTGTCCGAGAGGGAGACAGCTCCGTT
AT
<----------------------TCR Vα (TRAV5/TRAVJ36)--------------
--

------CDR1---------
AAACTGCACTTACACAGACAGCTCCTCCACCTACTTATACTGGTATAAGCAAGAATC
TG
------------------------TCR Vα----------------------------
--

------CDR2---------
GAGCAGGTCTCCAGTTGCTGACGTATATTTTCTCAAATATGGACATGAAACAAGACC
AA
------------------------TCR Vα----------------------------
--

AGACTCACTGTTCTATTGAATAAAAGGATAAACATCTGTCTCTGCGCATTGCAGAC
AC
------------------------TCR Vα----------------------------
--

------------CDR3----------
--
CCAGACTGGGGACTCAGCTATCTACTTCTGTGCAGAGACTTATCAAACTGGGGCAAA
CA
```

Figure 2A (cont.). AL9scTCR wild type nucleic acid sequence (CDRs italicized)

```
-------------------------TCR Vα------------------------------
---------
ACCTCTTCTTTGGGACTGGAACGAGACTCACCGTTATTCCCACTAGTGGAGGGGGTGGA
----TCR Vα-------------------------------><---Linker---------

AGCGGGGGTGGTGCTAGCGGTGGCGGCGGTTCTGGCGGTGGCGGTTCCTCAAGCGAAGC
-------------------------Linker---------------------------><---

TGGAGTTACTCAGTTCCCCAGCCACAGCGTAATAGAGAAGGGCCAGACTGTGACTCTGA
-------------------------TCR Vβ(TRBV14/TRBJ2-1)------------------

------CDR1------
GATGTGACCCAATT*TCTGGACATGATAAT*CTTTATTGGTATCGACGTGTTATGGGAAAA
-------------------------TCR Vβ------------------------------
```

Figure 2A (cont.). AL9scTCR wild type nucleic acid sequence (CDRs italicized)

```
        ------CDR2----------
GAAATAAAATTTCTGTTACATTTTGTGAAAGAGTCTAAACAGGATGAGTCCGGTATG
CC
-------------------------TCR Vβ----------------------------
--
```

```
CAACAATCGATTCTTAGCTGAAAGGACTGGAGGGACGTATTCTACTCTGAAGGTGCA
GC
------------------------TCR Vβ-----------------------------
--
```

```
                              ----------CDR3----------
--
CTGCAGAACTGGAGGATTCTGGAGTTTATTTCTGTGCCAGCAGCCAAGGGGTGACTT
TG
-----------------------------TCR Vβ------------------------
--
```

```
--CDR3----------
TTGAATGAGCAGTTCTTCGGGCCAGGGACACGGCTCACCGTGCTAGAGGACCTGAAC
AA
----------------------------TCR Vβ-------------><---TCR Cβ-----
```

```
GGTGTTCCCACCCGAGGTCGCTGTGTTTGAGCCATCAGAAGCAGAGATCTCCCACAC
CC
```

Figure 2A (cont.). AL9scTCR wild type nucleic acid sequence (CDRs italicized)

---------------------------TCR Cβ----------------------------

AAAAGGCCACACTGGTGTGCCTGGCCACAGGCTTCTTCCCTGACCACGTGGAGCTGAGC

---------------------------TCR Cβ----------------------------

TGGTGGGTGAATGGGAAGGAGGTGCACAGTGGGGTCAGCACGGACCCGCAGCCCCTCAA

---------------------------TCR Cβ----------------------------

GGAGCAGCCCGCCCTCAATGACTCCAGATACTGCCTGAGCAGCCGCCTGAGGGTCTCGG

---------------------------TCR Cβ----------------------------

CCACCTTCTGGCAGAACCCCCGCAACCACTTCCGCTGTCAAGTCCAGTTCTACGGGCTC

---------------------------TCR Cβ----------------------------

TCGGAGAATGACGAGTGGACCCAGGATAGGGCCAAACCCGTCACCCAGATCGTCAGCGC

---------------------------TCR Cβ----------------------------

Figure 2A (cont.). AL9scTCR wild type nucleic acid sequence (CDRs italicized)

CGAGGCCTGGGGTAGAGCAGAC (SEQ ID NO: 6)

--------TCR Cβ--------->

Figure 2B. AL9scTCR single mutant nucleic acid sequence

GGAGAGGATGTGGAGCAGAGTCTTTTCCTGAGTGTCCGAGAGGGA
GACAGCTCCGTTATAAACTGCACTTACACAGACAGCTCCTCCACCTACTTA
TACTGGTATAAGCAAGAATCTGGAGCAGGTCTCCAGTTGCTGACGTATAT
TTTCTCAAATATGGACATGAAACAAGACCAAAGACTCACTGTTCTATTGA
ATAAAAGGATAAACATCTGTCTCTGCGCATTGCAGACACCCAGACTGGG
GACTCAGCTATCTACTTCTGTGCAGAGACTCATCAAACTGGGGCAAACAA
CCTCTTCTTTGGGACTGGAACGAGACTCACCGTTATTCCCACTAGTGGAGG
GGGTGGAAGCGGGGGTGGTGCTAGCGGTGGCGGCGGTTCTGGCGGTGGC
GGTTCCTCAAGCGAAGCTGGAGTTACTCAGTTCCCCAGCCACAGCGTAAT
AGAGAAGGGCCAGACTGTGACTCTGAGATGTGACCCAATTTCTGGACATG
ATAATCTTTATTGGTATCGACGTGTTATGGGAAAAGAAATAAAATTTCTGT
TACATTTGTGAAAGAGTCTAAACAGGATGAGTCCGGTATGCCCAACAAT
CGATTCTTAGCTGAAAGGACTGGAGGGACGTATTCTACTCTGAAGGTGCA
GCCTGCAGAACTGGAGGATTCTGGAGTTTATTTCTGTGCCAGCAGCCAAG
GGGTGACTTTGTTAATGAGCAGTTCTTCGGGCCAGGGACACGGCTCACC
GTGCTAGAGGACCTGAACAAGGTGTTCCCACCCGAGGTCGCTGTGTTTGA
GCCATCAGAAGCAGAGATCTCCCACACCCAAAAGGCCACACTGGTGTGCC
TGGCCACAGGCTTCTTCCCTGACCACGTGGAGCTGAGCTGGTGGGTGAAT
GGGAAGGAGGTGCACAGTGGGGTCAGCACGGACCCGCAGCCCCTCAAGG
AGCAGCCCGCCCTCAATGACTCCAGATACTGCCTGAGCAGCCGCCTGAGG
GTCTCGGCCACCTTCTGGCAGAACCCCGCAACCACTTCCGCTGTCAAGTC
CAGTTCTACGGGCTCTCGGAGAATGACGAGTGGACCCAGGATAGGGCCAA
ACCCGTCACCCAGATCGTCAGCGCCGAGGCCTGGGGTAGAGCAGAC (SEQ ID NO: 7)

Figure 2C. AL9scTCR double mutant nucleic acid sequence

GGAGAGGATGTGGAGCAGAGTCTTTTCCTGAGTGTCCGAGAGGGA
GACAGCTCCGTTATAAACTGCACTTACACAGACAGCTCCTCCACCTACTTA
TACTGGTATAAGCAAGAACCGGGAGCAGGTCTCCAGTTGCTGACGTATAT
TTTCTCAAATATGGACATGAAACAAGACCAAAGACTCACTGTTCTATTGA
ATAAAAGGATAAACATCTGTCTCTGCGCATTGCAGACACCCAGACTGGG
GACTCAGCTATCTACTTCTGTGCAGAGACTCATCAAACTGGGGCAAACAA
CCTCTTCTTTGGGACTGGAACGAGACTCACCGTTATTCCCACTAGTGGAGG
GGGTGGAAGCGGGGGTGGTGCTAGCGGTGGCGGCGGTTCTGGCGGTGGC
GGTTCCTCAAGCGAAGCTGGAGTTACTCAGTTCCCCAGCCACAGCGTAAT
AGAGAAGGGCCAGACTGTGACTCTGAGATGTGACCCAATTTCTGGACATG
ATAATCTTTATTGGTATCGACGTGTTATGGGAAAAGAAATAAAATTTCTGT
TACATTTGTGAAAGAGTCTAAACAGGATGAGTCCGGTATGCCCAACAAT
CGATTCTTAGCTGAAAGGACTGGAGGGACGTATTCTACTCTGAAGGTGCA
GCCTGCAGAACTGGAGGATTCTGGAGTTTATTTCTGTGCCAGCAGCCAAG
GGGTGACTTTGTTGAATGAGCAGTTCTTCGGGCCAGGGACACGGCTCACC
GTGCTAGAGGACCTGAACAAGGTGTTCCCACCCGAGGTCGCTGTGTTTGA
GCCATCAGAAGCAGAGATCTCCCACACCCAAAAGGCCACACTGGTGTGCC
TGGCCACAGGCTTCTTCCCTGACCACGTGGAGCTGAGCTGGTGGGTGAAT
GGGAAGGAGGTGCACAGTGGGGTCAGCACGGACCCGCAGCCCCTCAAGG
AGCAGCCCGCCCTCAATGACTCCAGATACTGCCTGAGCAGCCGCCTGAGG
GTCTCGGCCACCTTCTGGCAGAACCCCGCAACCACTTCCGCTGTCAAGTC
CAGTTCTACGGGCTCTCGGAGAATGACGAGTGGACCCAGGATAGGGCCAA
ACCCGTCACCCAGATCGTCAGCGCCGAGGCCTGGGGTAGAGCAGAC (SEQ
ID NO: 8)

Figure 3A. Leader sequence

METDTLLLWVLLLWVPGSTG (SEQ ID NO: 9)

Figure 3B. Various protein domains for soluble fusion proteins

BirA
GGLNDIFEAQKIEWHE (SEQ ID NO: 10)

IL-2:
APTSSSTKKTQLQLEHLLLDLQMILNGINNYKNPKLTRMLTFKFYMPKKATELKHLQ
CLEEELKPLEEVLNLAQSKNFHLRPRDLISNINVIVLELKGSETTFMCEYADETATI
VEFLNRWITFCQSIISTLT (SEQ ID NO: 11)

IgG1:
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK (SEQ ID NO:
12)

IL-15:
NWVNVISDLKKIEDLIQSMHIDATLYTESDVHPSCKVTAMKCFLLELQVISLESGDA
SIHDTVENLIILANNSLSSNGNVTESGCKECEELEEKNIKEFLQSFVHIVQMFINTS
(SEQ ID NO: 13)

IL-15Rα sushi:
ITCPPPMSVEHADIWVKSYSLYSRERYICNSGFKRKAGTSSLTECVLNKATNVAHWT
TPSLKCIR (SEQ ID NO: 14)

INF-α:
CDLPQTHSLGSRRTLMLLAQMRRISLFSCLKDRHDFGFPQEEFGNQFQKAETIPVLH
EMIQQIFNLFSTKDSSAAWDETLLDKFYTELYQQLNDLEACVIQGVGVTETPLMKED
SILAVRKYFQRITLYLKEKKYSPCAWEVVRAEIMRSFSLSTNLQESLRSKE    (SEQ
ID NO: 15)

GM-CSF:
APARSPSPSTQPWEHVNAIQEARRLLNLSRDTAAEMNETVEVISEMFDLQEPTCLQT
RLELYKQGLRGSLTKLKGPLTMMASHYKQHCPPTPETSCATQTITFESFKENLKDFL
LVIPFDCWEPVQE (SEQ ID NO: 16)

Figure 3C. Various linker sequences

TSGGGGSGGGASGGGGSGGGGSSS (SEQ ID NO: 17);

GGGGSGGGGSGGGGSGGGGS (SEQ ID NO: 18);

VNAKTTAPSVYPLAPVS (SEQ ID NO: 19)

Figure 4A. Leader nucleic acid sequence

ATGGAGACAGACACACTCCTGTTATGGGTACTGCTGCTCTGGGTTCCAGGTTCCACCGGT (SEQ ID NO: 20)

Figure 4B. Fusion domain nucleic acid sequences

BirA:
GGTGGTCTGAACGACATCTTCGAAGCTCAGAAAATTGAATGGCACGAA (SEQ ID NO: 21)

IL-2:
GCACCTACTTCAAGTTCTACAAAGAAAACACAGCTACAACTGGAGCATTTACTGCTG
GATTTACAGATGATTTTGAATGGAATTAATAATTACAAGAATCCCAAACTCACCAGG
ATGCTCACATTTAAGTTTTACATGCCCAAGAAGGCCACAGAACTGAAACATCTTCAG
TGTCTAGAAGAAGAACTCAAACCTCTGGAGGAAGTGCTAAATTTAGCTCAAAGCAAA
AACTTTCACTTAAGACCCAGGGACTTAATCAGCAATATCAACGTAATAGTTCTGGAA
CTAAAGGGATCTGAAACAACATTCATGTGTGAATATGCTGATGAGACAGCAACCATT
GTAGAATTTCTGAACAGATGGATTACCTTTTGTCAAAGCATCATCTCAACACTAACT
(SEQ ID NO: 22)

IgG1:
GCCTCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGCTGTCCTA
CAGTCCTCAGGACTCTACTCCCTCAGCAGCGTGGTGACCGTGCCCTCCAGCAGCTTG
GGCACCCAGACCTACATCTGCAACGTGAATCACAAGCCCAGCAACACCAAGGTGGAC
AAGAAAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAG
ACAAAGCCGCGGGAGGAGCAGTACAACAGCACGTACCGGGTGGTCAGCGTCCTCACC
GTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAA
CCACAGGTGTACACCCTGCCCCCATCCCGGGATGAGCTGACCAAGAACCAGGTCAGC
CTGACCTGCCTGGTCAAAGGCTTCTATCCCAGCGACATCGCCGTGGAGTGGGAGAGC
AATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGC
CTCTCCCTGTCTCCGGGTAAA (SEQ ID NO: 23)

IL-15:
AACTGGGTGAATGTAATAAGTGATTTGAAAAAAATTGAAGATCTTATTCAATCTATG
CATATTGATGCTACTTTATATACGGAAAGTGATGTTCACCCCAGTTGCAAAGTAACA
GCAATGAAGTGCTTTCTCTTGGAGTTACAAGTTATTTCACTTGAGTCCGGAGATGCA
AGTATTCATGATACAGTAGAAAATCTGATCATCCTAGCAAACAACAGTTTGTCTTCT
AATGGGAATGTAACAGAATCTGGATGCAAAGAATGTGAGGAACTGGAGGAAAAAAAT
ATTAAAGAATTTTTGCAGAGTTTTGTACATATTGTCCAAATGTTCATCAACACTTCT
(SEQ ID NO: 24)

IL-15Rα sushi:
ATCACGTGCCCTCCCCCCATGTCCGTGGAACACGCAGACATCTGGGTCAAGAGCTAC
AGCTTGTACTCCAGGGAGCGGTACATTTGTAACTCTGGTTTCAAGCGTAAAGCCGGC
ACGTCCAGCCTGACGGAGTGCGTGTTGAACAAGGCCACGAATGTCGCCCACTGGACA
ACCCCCAGTCTCAAATGCATTAGA (SEQ ID NO: 25)

Figure 4B (cont.). Fusion domain nucleic acid sequences

INF-α
TGTGATCTGCCTCAAACCCACAGCCTGGGTAGCAGGAGGACCTTGATGCTCCTGGCA
CAGATGAGGAGAATCTCTCTTTTCTCCTGCTTGAAGGACAGACATGACTTTGGATTT
CCCCAGGAGGAGTTTGGCAACCAGTTCCAAAAGGCTGAAACCATCCCTGTCCTCCAT
GAGATGATCCAGCAGATCTTCAATCTCTTCAGCACAAAGGACTCATCTGCTGCTTGG
GATGAGACCCTCCTAGACAAATTCTACACTGAACTCTACCAGCAGCTGAATGACCTG
GAAGCCTGTGTGATACAGGGGGTGGGGGTGACAGAGACTCCCCTGATGAAGGAGGAC
TCCATTCTGGCTGTGAGGAAATACTTCCAAAGAATCACTCTCTATCTGAAAGAGAAG
AAATACAGCCCTTGTGCCTGGGAGGTTGTCAGAGCAGAAATCATGAGATCTTTTTCT
TTGTCAACAAACTTGCAAGAAAGTTTAAGAAGTAAGGAA (SEQ ID NO: 26)

GM-CSF:
GCACCCGCCCGCTCGCCCAGCCCCAGCACGCAGCCCTGGGAGCATGTGAATGCCATC
CAGGAGGCCCGGCGTCTCCTGAACCTGAGTAGAGACACTGCTGCTGAGATGAATGAA
ACAGTAGAAGTCATCTCAGAAATGTTTGACCTCCAGGAGCCGACCTGCCTACAGACC
CGCCTGGAGCTGTACAAGCAGGGCCTGCGGGGCAGCCTCACCAAGCTCAAGGGCCCC
TTGACCATGATGGCCAGCCACTACAAGCAGCACTGCCCTCCAACCCCGGAAACTTCC
TGTGCAACCCAGACTATCACCTTTGAAAGTTTCAAAGAGAACCTGAAGGACTTTCTG
CTTGTCATCCCCTTTGACTGCTGGGAGCCAGTCCAGGAG (SEQ ID NO: 27)

Figure 4C. Linker nucleic acid sequences

ACTAGTGGAGGGGGTGGAAGCGGGGGTGGTGCTAGCGGTGGCGGCGGTTCTGGCGGTGGCGGTTCCTCAAGC (SEQ ID NO: 28);

GGTGGCGGTGGCAGCGGCGGTGGTGGTTCCGGTGGCGGCGGTTCTGGCGGTGCGGTTCC (SEQ ID NO: 29);

GTTAACGCAAAGACAACCGCCCCTTCAGTATATCCACTAGCGCCCGTT (SEQ ID NO: 30)

Figure 9.
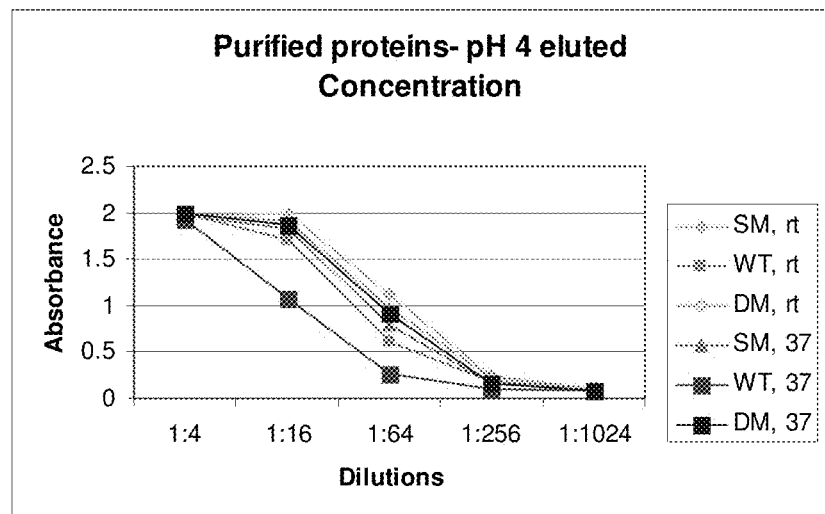
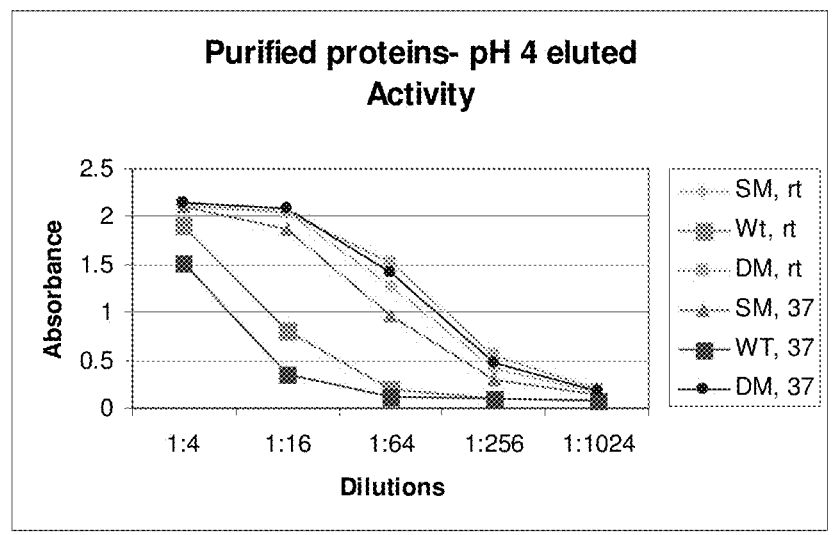

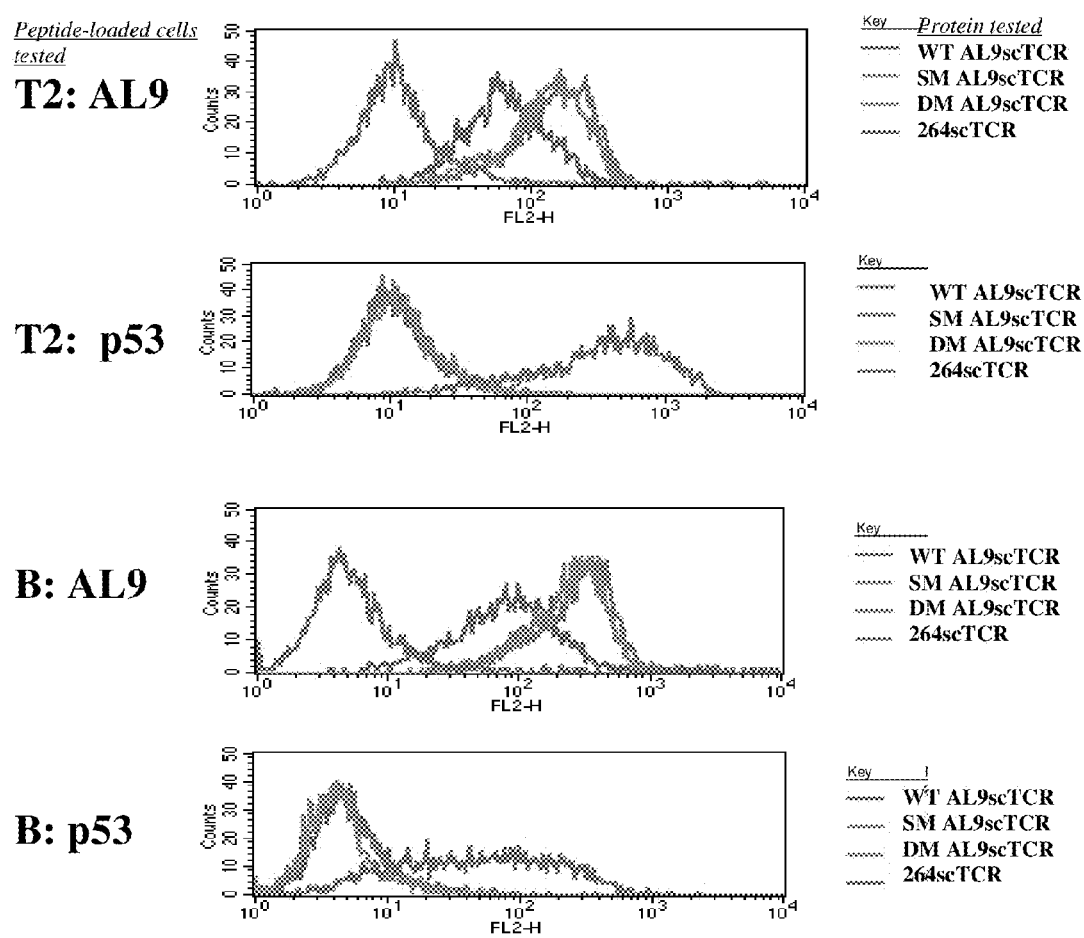

Figure 10D.
*Peptides tested in antigen presenting cells*
Gag p17 peptide
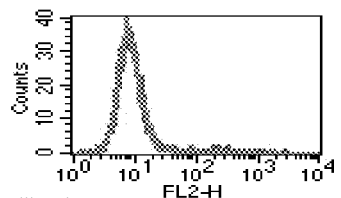
Pol
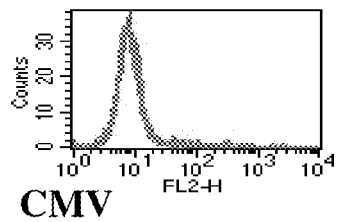
CMV
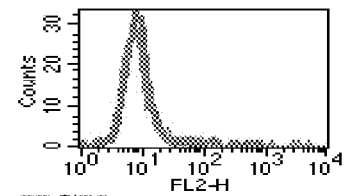
HCV core
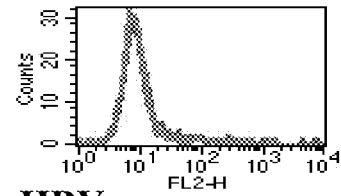
HBV env
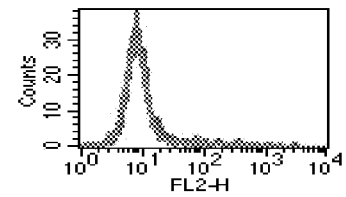
p53 264-272
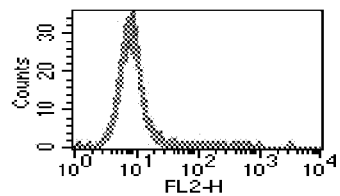
MART-1
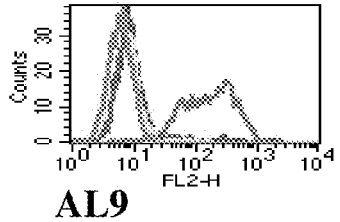
AL9
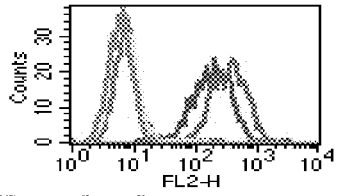
Unpulsed
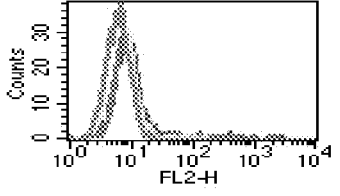
Key  *Proteins tested*
— Wt AL9scTCR
— SM AL9scTCR
— MART-1scTCR
— SA-PE
— Unstained

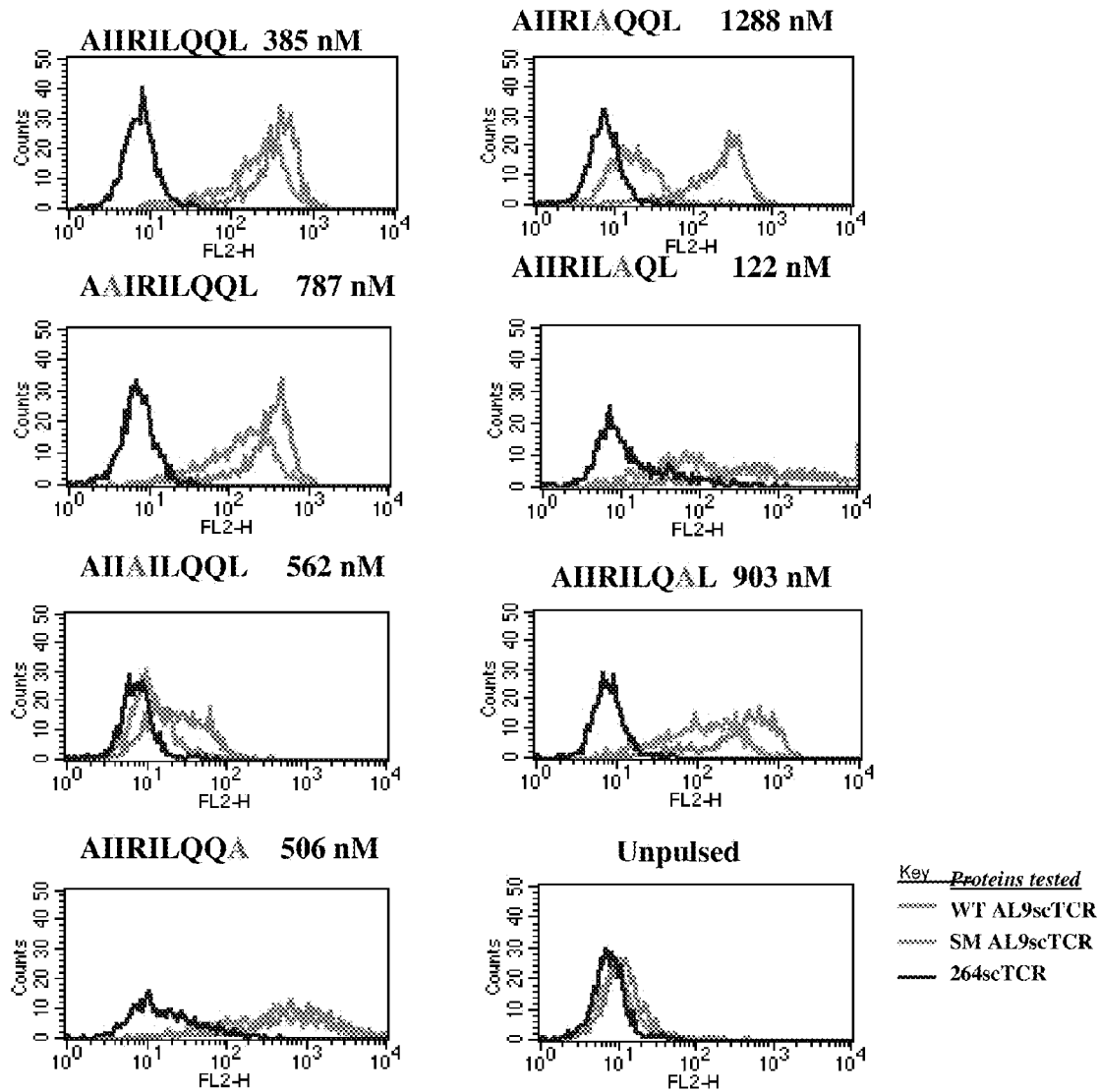
Figure 13. (SEQ ID NOS 1 and 31-36, respectively, in order of appearance)

Figure 14A. ("ALIRILQQL" disclosed as SEQ ID NO: 37 and "AIIRILQQL" disclosed as SEQ IN NO: 1)

| Subject or parameter | Amino acid at position: | | | | | | | | |
|---|---|---|---|---|---|---|---|---|---|
| | 59 (A)[b] | 60 (I) | 61 (I) | 62 (R) | 63 (I) | 64 (L) | 65 (Q) | 66 (Q) | 67 (L) |
| AC-01 | A | I | I | R | I | L | Q | Q | L |
| AC-03 | A | I | I | R | I | L | Q | Q | L |
| AC-07 | A | I | I | R | M[e] | L | Q | Q | L |
| AC-09 | A | I | I | R | I | L | Q | Q | L |
| AC-26 | A | I | I | R | I | L | Q | Q | L |
| AC-29 | A | I | I | R | T | L | Q | Q | L |
| AC-34 | A | I | I | R | I | L | Q | Q | L |
| AC-35 | A | I | I | R | L | L | Q | Q | L |
| AC-41 | A | I | I | R | T | L | Q | Q | L |
| AC-59 | A | I | I | R | T | L | Q | Q | L |
| AC-04[a] | A | L | I | R | I | L | Q | Q | L |
| AC-13[a] | A | L | I | R | I | L | Q | Q | L |
| AC-60[d] | A | L | I | R | I | L | Q | Q | L |
| AC-75[a] | A | L | I | R | I | L | Q | Q | L |
| % Conservation[c] | 98.6 | 81.9 | 96.4 | 97.8 | 77.6 | 100 | 99.3 | 100 | 97.8 |

[a] Individual who developed a CD8+ T-cell response directed against the Vpr$_{59-67}$ epitope.
[b] Letters in parentheses represent amino acids in the HIV-1 clade B 2002 consensus sequence (http://hiv-web.lanl.gov).
[c] Percent conservation was calculated by aligning the Vpr$_{59-67}$ epitope with the published HIV-1 clade B sequence (http://hiv-web.lanl.gov).
[d] Sequences of 16 individual clones demonstrated a mixed viral population of ALIRILQQL (n = 10) and AIIRILQQL (n = 6) sequences (differences are underlined).
[e] Bold type represents amino acids that differ from the HIV-1 clade B consensus sequence.

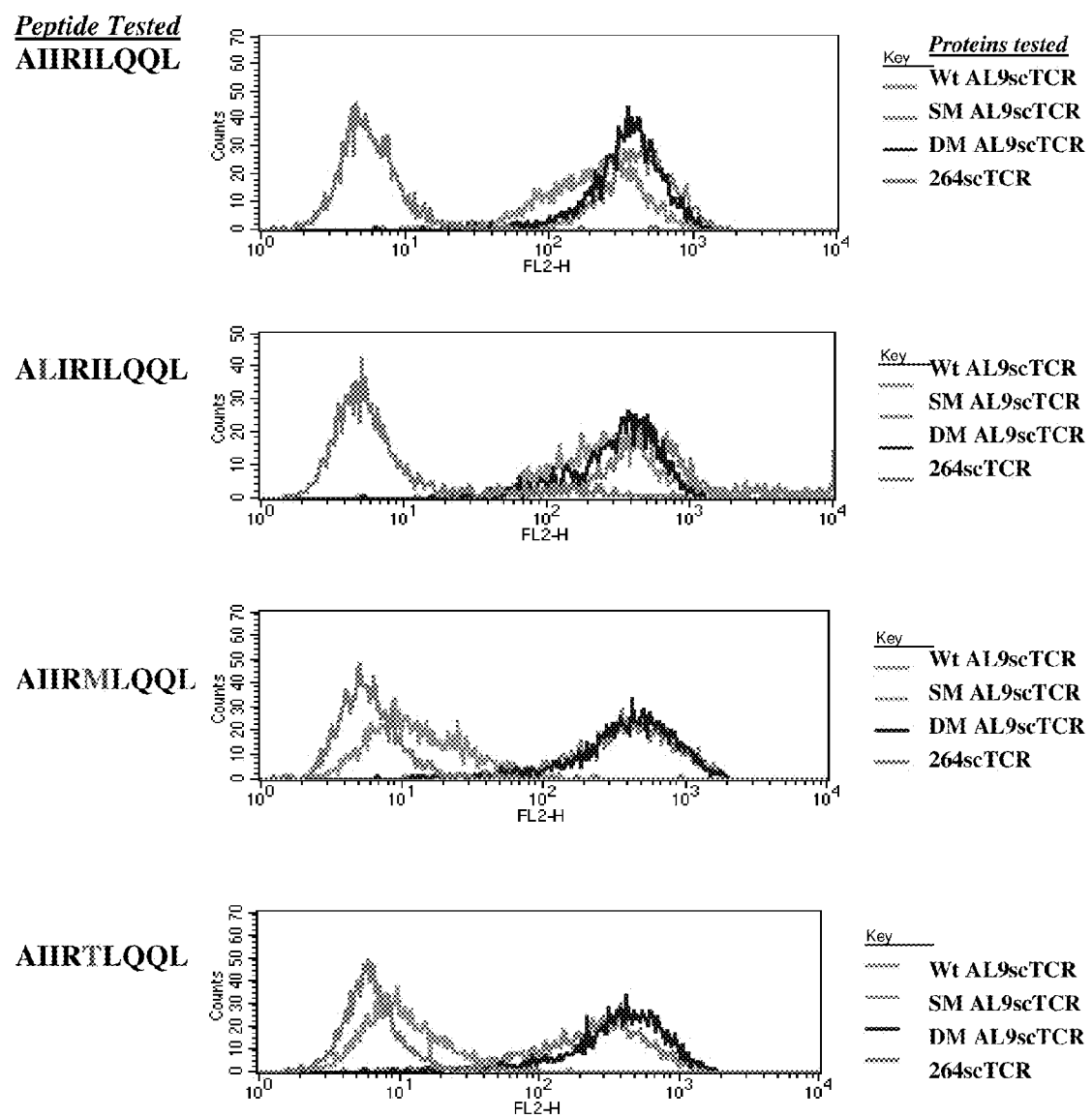
Figure 14B. (SEQ ID NOS 1 and 37-39, respectively, in order of appearance)

Figure 14B (cont.) (SEQ ID NOS 40-41, 1, 42-43, 38, 31 and 44, respectively, in order of appearance)
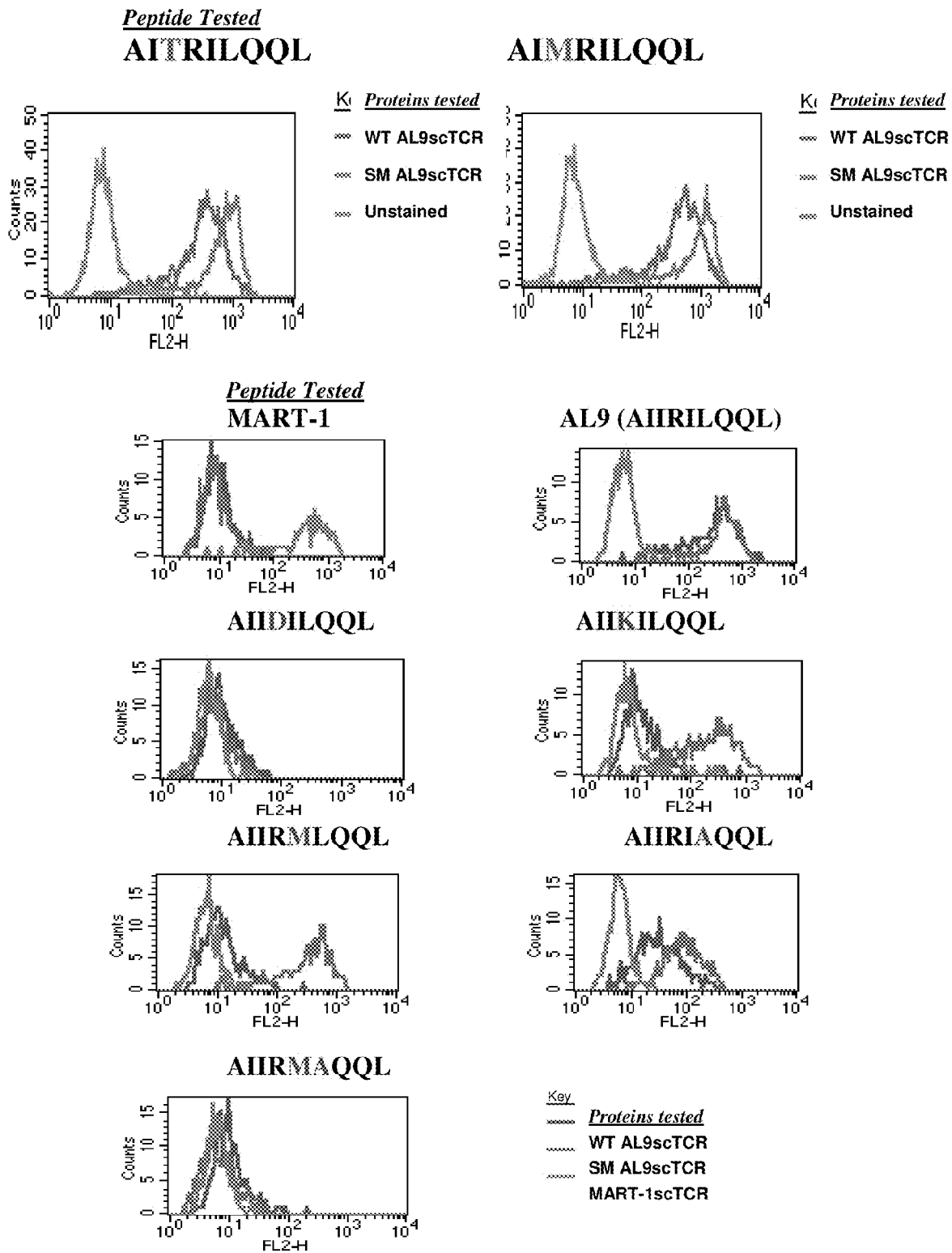

Figure 14B (cont.) (SEQ ID NOS 1, 31, 38 and 43, respectively, in order of appearance)
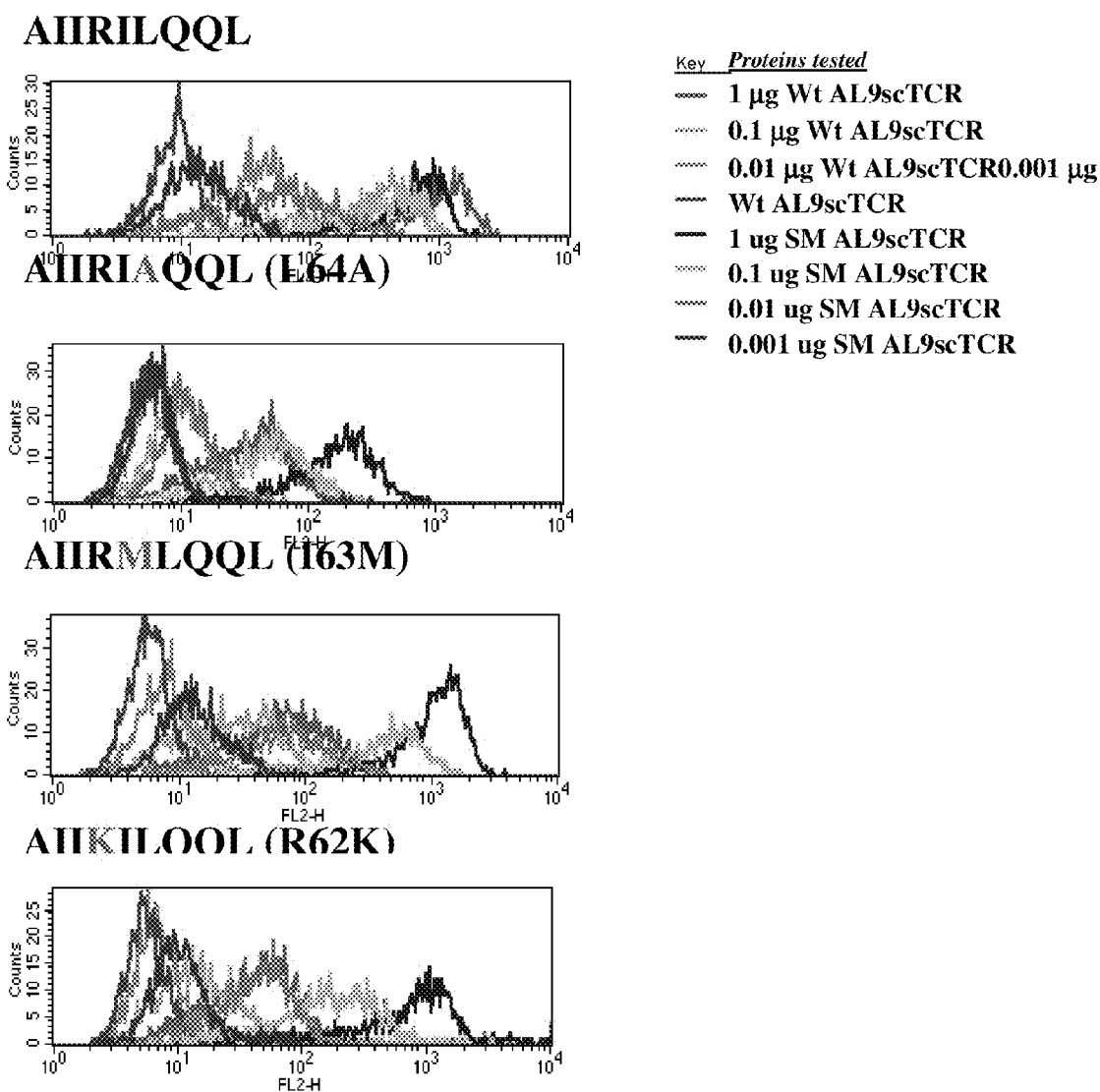

HIV VPR-SPECIFIC T-CELL RECEPTORS

RELATED APPLICATIONS

This application is a divisional application of U.S. Ser. No. 12/731,485, filed Mar. 25, 2010, which claims the benefit under 35 U.S.C. §119(e) of U.S. Provisional Application No. 61/163,421, filed Mar. 25, 2009, the entire contents of each of which are incorporated herein by reference.

SEQUENCE LISTING

The instant application contains a Sequence Listing which has been submitted via EFS-Web and is hereby incorporated by reference in its entirety. Said ASCII copy, created on Apr. 28, 2010, is named 83717.txt and is 35,656 bytes in size.

BACKGROUND OF THE INVENTION

Current approaches for treating HIV infection are primarily aimed at limiting viral replication or infectivity but do not target latent virus or virally infected cells. As a result of HIV's high mutation rate, drug resistant variants emerge from the latent viral reservoir leading to disease progression in treated patients and infection of other individuals. Several studies have shown that viral escape from CTL responses commonly occurs during the course of the infection. Escape variants may arise through the selection of sequence variations in positions that are important for binding to MHC or in positions that are responsible for interaction between the TCR and the peptide-MHC complex. Circumventing these viral CTL escape mutations is important for eliciting an effective CTL response and for the development of vaccines against HIV-1.

Accordingly, the need exists for therapeutic agents that can effectively target not only the wide-type HIV but also variants that develop during the course of infection.

SUMMARY OF THE INVENTION

The instant inventors have discovered TCR molecules that bind to peptides derived from the vpr protein of HIV when presented in their cognate MHC complex. Specifically, the instant inventors have made mutations in these TCRs that allow the resulting TCR molecules to bind to variants of the vpr peptide epitope, while still binding to the consensus vpr peptide epitope. In a specific embodiment, the inventors have made mutant TCRs that bind to the AL9 consensus epitope of vpr (AIIRILQQQL (SEQ ID NO: 1), amino acids 59-67) with improved binding affinity, while also binding common variants of this epitope.

Accordingly, in one aspect, the invention provides an isolated T cell receptor (TCR) that specifically binds an HIV epitope from HIV-1 vpr, comprising at least one mutation in the wild type TCR Vα or Vβ sequence of set forth in FIG. 1. In one embodiment, the mutation increases the productivity, stability, specific binding activity, or functional activity of the TCR. In another embodiment, the mutation reduces the non-specific binding of the TCR mutant compared to the wild type TCR. In specific embodiments, the TCR is a single-chain TCR or a heterodimeric TCR. In one embodiment, the TCR comprises more than one TCR binding domain.

In one embodiment, the TCRs of the invention recognize the AL9 peptide (AIIRILQQL (SEQ ID NO: 1)) of vpr. In another embodiment, the AL9 peptide is presented in the context of HLA-A2.

In one embodiment, the mutation is at amino acid residue 39 in the TCR Vα chain of the TCR. In another embodiment, the mutation is at amino acid residue 93 in the TCR Vα chain. In a specific embodiment, the mutation at amino acid residue 39 is Ser to Pro. In another specific embodiment, the mutation at amino acid residue 93 is Tyr to His, Leu, Lys, Gln, or Ala.

In another embodiment, the TCRs of the invention specifically bind to one or more HIV-1 vpr AL9 peptide variants. In one embodiment, the TCRs of the invention bind the AL9 peptide variants in the context of HLA-A2. In a related embodiment, the AL9 peptide variants comprise one or more amino acid changes within the AL9 peptide sequence.

In another embodiment, the TCRs of the invention have greater stability at elevated temperatures than the wild type TCR. In preferred embodiments of the invention, the TCRs are soluble.

In a specific embodiment, the invention provides an isolated single chain T cell receptor (TCR) that specifically binds to the AL9 peptide from HIV-1 vpr. In one embodiment the scTCR recognizes the AL9 epitope. In one embodiment, the scTCR has a one or more mutations in the Vα chain as compared to the wild-type sequence set forth in FIG. 1.

In another embodiment, the TCR further comprises a functional polypeptide domain, diagnostic/imaging agent, drug-containing nanoparticle, therapeutic agent, cytotoxic agent or an anti-viral agent. In exemplary embodiments, the functional polypeptide domain comprises a cytokine, immunoglobulin domain, receptor domain or polypeptide tag sequence. In another exemplary embodiment, the cytokine comprises IL-2, IL-15, GM-CSF, interferon, the immunoglobulin domain comprises IgG1 constant regions or Ig Fc domains, or a fragment thereof. In another exemplary embodiment, the polypeptide tag comprises the birA sequence.

In another embodiment, the TCR further comprises a transmembrane domain allowing cell surface expression of the TCR. In one embodiment, the TCR further comprises a cytoplasmic domain, wherein the cytoplasmic domain allows intracellular signaling in response to interactions between the TCR mutant and the HIV epitope. In one embodiment, the TCR comprises transmembrane and/or cytoplasmic signaling domains from CD3, CD28, CD8, 4-1BB, Ox-40, ICOS and/or Lck proteins. Alternatively, the TCR can comprise TCR transmembrane and/or TCR cytoplasmic signaling domains. Various soluble and membrane bound fusion proteins have been disclosed previously (Card et al. 2004 Cancer Immunol Immunother. 53:345; Mosquera et al. 2005 J. Immunol. 174:4781; Zhu X et al. 2006 J. Immunol. 176:3223; Belmont et al. 2006 Clin. Immunol. 121:29; Finney et al. 2004. J. Immunol. 172: 104; Brentjens et al. 2007 Clin Cancer Res. 13, 5426; Zhang et al. 2004. Cancer Gene Therapy 11, 487).

In another embodiment, the mutation further increases the activity of the TCR to detect cells presenting an HIV epitope compared to the wild type TCR. In another embodiment, the mutation increases the cytotoxic functional activity of the TCR against cells presenting an HIV epitope as compared to the wild type TCR.

In another embodiment, the invention provides nucleic acid molecules encoding the TCRs of the invention, e.g., such as those presented in FIG. 2. In one embodiment, the invention provides expression vectors comprising the nucleic acid molecules of the invention. In yet another related embodiment, the invention provides host cells comprising the expression vector of the invention. In one embodiment, the host cell is mammalian host cell, e.g., a human cell.

In one aspect, the invention provides methods for detecting cells infected with HIV by contacting a cell with the TCR of the invention and determining if the TCR binds to the cell, wherein TCR binding to the cell is indicative of HIV infection.

In another aspect, the invention provides methods of killing a cell infected with HIV by contacting the cell with a TCR of the invention, thereby killing the cell infected with HIV.

In another aspect, the invention provides methods for determining if a subject is infected with HIV by obtaining a biological sample from an individual and contacting the biological sample with a TCR of the invention, wherein binding of the TCR to the biological sample is indicative of the subject being infected with HIV.

In another aspect, the invention provides methods for treating a subject having HIV by administering to the individual a TCR of the invention or a nucleic acid, vector of the invention or host cell of the invention, thereby treating the subject.

In another aspect, the invention provides methods for inhibiting HIV infection in a subject by administering to the individual a TCR of the invention, the nucleic acid or vector of the invention or host cell of the invention—thereby inhibiting HIV infection in a subject.

In related embodiment, the methods further comprise identifying a subject with an increased risk of HIV infection.

In another aspect, the invention provides pharmaceutical compositions comprising a TCR of the invention and a pharmaceutically acceptable carrier.

In another aspect, the invention provides kits comprising a TCR of the invention and instructions for use.

DESCRIPTION OF THE DRAWINGS

FIG. 1A sets forth the AL9scTCR wild type protein sequence (CDRs italicized).

FIG. 1B sets forth the AL9scTCR single mutant (Y93H) protein sequence.

FIG. 1C sets forth the AL9scTCR double mutant (S39P, Y93H) protein sequence.

FIG. 2A sets forth the AL9scTCR wild type nucleic acid sequence (CDRs italicized).

FIG. 2B sets forth the AL9scTCR single mutant nucleic acid sequence.

FIG. 2C sets forth the AL9scTCR double mutant nucleic acid sequence.

FIG. 3A sets forth exemplary leader sequences.

FIG. 3B sets forth various protein domains.

FIG. 3C sets forth various linker sequences.

FIG. 4A depicts leader nucleic acid sequence.

FIG. 4B depicts fusion domain nucleic acid sequences.

FIG. 4C shows a variety of linker nucleic acid sequences.

FIG. 9 is a characterization of purified AL9scTCR sm and dm proteins.

FIG. 10C depicts the binding of wt, sm and dm AL9scTCR multimers to T2 or B cells loaded with AL9 or p53 (control) peptide.

FIG. 10D depicts the lack of binding of wt and sm AL9scTCR multimers to non-specific peptides loaded on T2 cells.

FIG. 13 depicts the binding of wt and sm AL9scTCR multimers to T2 cells loaded with AL9 peptide mutants.

FIG. 14A depicts published analysis of the most frequently occurring vpr AL9 peptide variants (Altfeld et al. 2005. J. Virol. 79: 5000).

FIG. 14B depicts the flow cytometry analysis of the binding of wt, sm and dm AL9scTCR fusions to AL9 peptide variants compared to the AL9 consensus.

DETAILED DESCRIPTION OF THE INVENTION

Figure 5:
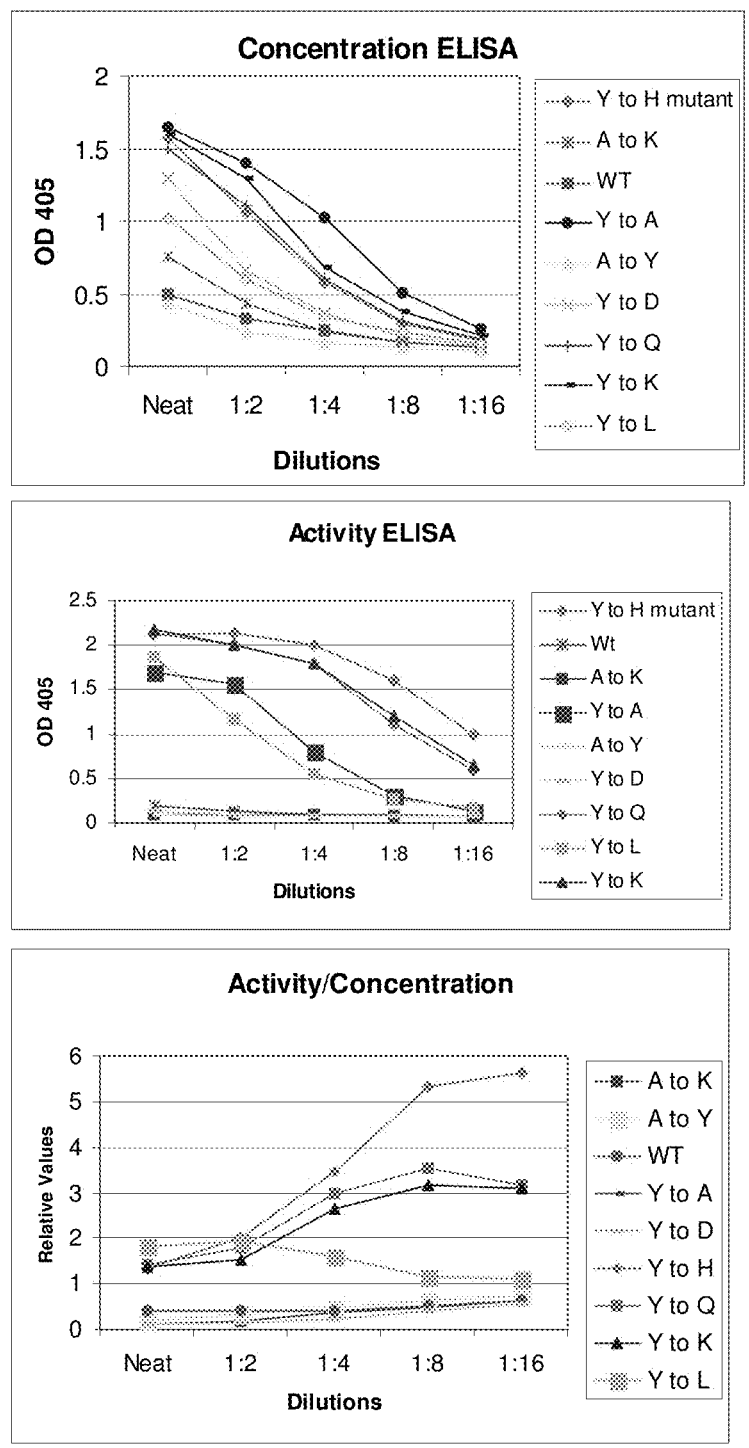
FIG. 5 is a characterization of Y93 and A97 CDR3 Vα mutations in AL9scTCR produced in HEK-293 cells.

The instant inventors have discovered TCR molecules that bind to peptides derived from the vpr protein of HIV when presented in their cognate MHC complex. Specifically, the instant inventors have identified TCRs that bind to the AL9 epitope of vpr (AIIRILQQQL (SEQ ID NO: 1), amino acids 59-67). Moreover, the inventors have identified variants of these TCRs that recognize a number of common variants that arise in the AL9 epitope during the course of infection by the virus. The data disclosed herein elucidates sequences for HIV-1-specific TCRs for diagnostic and therapeutic use.

Presently, recombinant HIV-1-specific antibodies are available for the direct targeting of HIV-1 infected cells. One drawback of the antibody approach is that only the envelope of the HIV-1 virus is accessible for HIV-1 antibodies, while the functionally most important HIV proteins are hidden inside the infected cell and only accessible to the immune system after intracellular processing and presentation by MHC class I or II molecules. Once presented by MHC molecules, these HIV gene products are recognized by TCRs, but not by antibodies. HIV-1 antibodies therefore only allow for a very limited targeting of HIV-1 infected cells. The compositions described herein provide a solution to this problem.

The soluble TCRs which are specific for HIV 1 have significant advantages over existing approaches.

The TCR sequences are useful for the production of recombinant single chain TCR that are able to specifically recognize HIV-1 infected cells. These recombinant TCR are practically used for (i) the in vivo targeting of HIV-1 infected cells in immunotherapeutic, gene transfer of cell-based therapeutic approaches, (ii) the ex vivo assessment of HIV-1 antigen expression on lymphocytes or professional antigen presenting cells. The quantitative analysis of HIV-1 antigen expression is important in studies on HIV-1 immunopathogenesis and are useful for the ex vivo screening/monitoring for preventative and therapeutic approaches.

Currently, treatment of HIV-1 infected patients is based on the use of antiretroviral drugs. These drugs are very effective, but have cumulative toxicity, are associated with high pill burdens and can lead to viral resistance. Therefore, there is a continuing need for other treatment options for these patients. Immunotherapeutic treatment approaches with soluble TCRs represent an alternative treatment option for the HIV-1 infected patient population. In addition, the TCR are used for the ex vivo assessment of HIV-1 antigen expression.

The TCRs described herein recognize a number of variants of the vpr gene that commonly arise during HIV infection allowing for increased efficacy for the molecules of the invention as compared to TCRs previously identified.

The invention features methods and compositions for diagnosis and treatment of viral infections. The methods are based on the identification of T-cell receptors that are specific for HIV-1. Specifically, the instant invention provides TCR molecules that specifically bind to an epitope of the vpr protein from HIV. The epitope comprises or consists of a short, 8 to 11-mer peptide that is found in the vpr protein. Specifically, the vpr epitope is AIIRILQQL (SEQ ID NO: 1) (amino acids 59-67) of the vpr protein.

The T cell receptors of the invention can be heteromultimeric molecules or can be single chain TCR molecules. The scTCRs comprise a Vα domain linked to Vβ/Cβ domains either directly or via a flexible linker. Specific molecules of the invention further comprise an additional polypeptide. In certain embodiments that contain this additional polypeptide, the Cβ domain is truncated just prior to the final cysteine.

The invention provides TCRs comprising one or more mutation in the variable regions that allows for the recognition of epitopes that contain one or more amino acid substitution. For example, the invention provides TCRs that bind not only to the consensus AL9 epitope of the vpr protein, but also to epitopes that comprise one, two or three amino acid substitutions in the AL9 epitope.

In exemplary embodiments, the TCRs of the invention recognize the AL9 epitope comprising mutations in at the position corresponding to amino acid number 60, 61, 62, or 63 of the vpr protein. In exemplary embodiments, one or more mutations in the Vα chain of the TCR allow for the recognition of variant vpr sequences.

Methods of Diagnosis

Soluble TCRs are used to analyze HLA-mediated presentation of cytotoxic T cell epitope presentation on professional antigen presenting cells or HIV infected cells. For example, a sample of bodily fluid, e.g., blood, or bodily tissue, e.g., lymph node, is obtained from a subject. Leukocytes from the sample are contacted with single chain TCRs described herein. To increase sensitivity, four single chain TCR constructs linked together, e.g., with a central streptavidin to form a tetrameric complex. The construct is linked to a detectable marker, e.g., it is labeled with a fluorescence fluorophore. Detectable markers include fluorochromes such as Phycoerythrin (PE), Fluorescein isothiocyanate (FITC), and Allophycocyanin (APC). Detection is carried out by flow cytometry and/or tissue staining (fluorescence microscopy or immunohistochemistry). In another example, a plurality of TCR constructs are immobilized in a microarray, e.g., a chip or plate, and a patient-derived sample is allowed to contact the array, the array is washed, and bound cells detected. In this manner, the peptide expressed or presented on the antigen presenting cell or HIV infected cell of a patient is determined. Thus, soluble TCRs are also useful as a research tool for the ex vivo assessment and quantification of HIV-1 epitope presentation. They are useful tools for identifying patients who express specific HIV-1 epitopes, e.g., the AL9 epitope of vpr, and are therefore promising candidates for immunotherapeutic interventions described herein.

Methods of Therapy

To treat patients infected with HIV, one or a mixture of soluble single chain TCR constructs are administered. In one embodiment, the TCRs of the invention induce antibody-dependent cell-mediated cytotoxicity (ADCC). ADCC provides an effective immune response to HIV infection. It has been associated with protection from simian immunodeficiency virus disease in macaques delayed progressive HIV infection in humans, protection of intravenous drug users from HIV-1 infection, and lower genital HIV viral loads. The ability of, for example, the high affinity AL9 scTCR Ig to mediate ADCC-like activity demonstrates that they could be used in a passive immune therapy approach to stimulate targeted, potent, innate immune responses against HIV-infected cells.

In an alternative embodiment, the TCRs further comprise a second composition such as a functional polypeptide domain, diagnostic/imaging agent, drug-containing nanoparticle, therapeutic agent, cytotoxic agent or anti-viral agent. In exemplary embodiments, functional polypeptide domain comprises a cytokine, immunoglobulin domain, receptor domain or polypeptide tag sequence. Exemplary cytokines are IL-2, IL-15, GM-CSF, or interferon, and exemplary immunoglobulin domain comprises IgG1 constant regions or Ig Fc domains, or a fragment thereof.

One advantage of such a construct is increased half-life and the antigen-specific delivery of these reagents directly to infected cells. This therapeutic strategy reduces the overall drug dose, the dosing frequency, and the treatment-associated side effects.

In an alternative embodiment, nucleic acids encoding the TCRs of the invention or cell expressing the TCRs of the invention can be used in gene transfer or cell-based approaches to kill HIV infected cells or to prevent or treat HIV infection. In one example, genes encoding TCRs of the invention could be transferred into immune cells such that the immune cells now expressed TCRs of the invention on the cell surface. These cells could then be activated to express immune functions when the TCR interacts with HIV vpr peptide displayed in the HLA-A2 complex. These cells could be used in killing HIV-infected cells ex vivo or, following infusion into patients with HIV infection, kill HIV infected cells in the patient. Alternatively, nucleic acids encoding the TCRs of the invention could be directly administered to the patients, thereby allowing gene transfer into the patient's immune cells and expression of the TCRs of the invention on these cells in vivo. Such cells could provide protective or therapeutic activity against HIV infection.

The TCRs of the invention can be delivered by methods known to one of skill in the art. For example, parenteral administration, such as intravenous, subcutaneous, intramuscular, and intraperitoneal delivery routes, may be used to deliver the TCRs. For instance, soluble TCR fusion have been intravenously injected into mice and humans at a dose of 0.015 to 10 mg/kg. Determination of patient doses is carried using methods wells known in the art.

The compositions of the invention can be administered to prevent or treat HIV infection or reduce the number of HIV-infected cell. Determination of the proper dosage and administration regime for a particular situation is within the skill of the art. An effective amount of a therapeutic protein is preferably from about 0.01 mg/kg to about 150 mg/kg. Effective doses vary, as recognized by those skilled in the art, depending on the nature of the therapeutic treatment (i.e. biologic, nucleic acid or cell-based), route of administration, excipient usage, and coadministration with other therapeutic treatments including use of other agents or therapeutic agents. A therapeutic regimen is carried out by identifying a mammal, e.g., a human patient suffering from (or at risk of developing) infection by a viral pathogen, using standard methods. The pharmaceutical compound is administered to such an individual using methods known in the art. Preferably, the compound is administered orally, rectally, nasally, topically or parenterally, e.g., subcutaneously, intraperitoneally, intrathecally, intramuscularly, and intravenously.

In the case of polypeptide sequences which contain mutations or substitutions as compared to the wild-type TCR sequence, the mutated positions are preferably, but not necessarily, conservative substitutions. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. In peptides in which amino acids substitutions are made relative to the wild-type TCR sequence, the resulting TCR molecules recognize one or more HIV peptides comprising one or more amino acid mutations. In specific embodiments, the HIV protein is vpr. In peptides in which amino acids substitutions are made relative to the wild-type TCR sequence, the binding affinity of the T-cell receptor to its HLA-restricted epitope is increased. Alternatively, constructs containing substitutions have great stability, e.g., a longer half-life in a physiologically acceptable solution such as culture media or a bodily fluid such as blood, plasma, or serum. For example, the binding affinity and/or stability of such derivative peptides is at least 5%, 10%, 25%, 50%, 75%, 90%, 100%, 2-fold, 5-fold, 10-fold, 20-fold, or more relative to that of the reference peptide sequence.

EXAMPLES

It should be appreciated that the invention should not be construed to be limited to the examples that are now described; rather, the invention should be construed to include any and all applications provided herein and all equivalent variations within the skill of the ordinary artisan.

Example 1

Generation of Single Chain TCR Constructs with Specific Mutations

CTLs from HLA-A2 Vpr, a 14 kD accessory protein of HIV, plays a crucial role in viral replication and suppression of the host immune response. It is one of the most frequently targeted proteins by CTL relative to the length of the protein. CD8+ T cell responses against Vpr were found in 45% of individuals (Altfeld et al. 2001, J. Immunol. 167: 2743). The HLA-A2.1-restricted Vpr epitope AIIRILQQL (SEQ ID NO: 1) (amino acids 59-67) (AL9 epitope) can represent a good early target for CD8+ T cells, in primary infection in a subset of HLA-A2 positive individuals. It is the most common current sequence within this epitope (consensus sequence) and is targeted with similar frequencies in individuals with acute (21%) and chronic (24%) infections (Altfeld et al. 2005. J. Virol. 79: 5000). Therapies targeted against vpr expressing cells could be potentially useful in eliminating HIV infected cells. However Altfeld et al also showed that individuals infected in the acute stage of infection with viruses containing the consensus sequence were unable to mount epitope-specific T cell responses, but subjects infected with the 160L variant all developed these responses. Variants of the AL9 epitope can arise frequently and need to be targeted by therapies designed to eliminate the virus.

Soluble T cell receptors could be used to effectively deliver therapeutic molecules to infected cells. The inherently low affinity (1-100 µM) of TCRs for cognate peptide MHC has been a major limitation for therapeutic and diagnostic applications. Contacts between TCR and peptide-MHC occur through the Vα CDR1, CDR2 and CDR3 and/or Vβ CDR1, CDR2 and CDR3 with the CDR3 domains making the most contacts with the peptide. Several studies have shown that mutation of residues within these regions can improve TCR affinity. High affinity variants of the 2C TCR, a mouse alloreactive TCR, were identified by yeast display following selection from a library of CDR3α mutants. Mutation of the CDR3 regions of TCRs specific for the NY-ESO-1 tumor associated antigen and the human T-cell lymphotropic virus type 1 (HTLV-1) tax peptide and their display on the surface of phage has also been used to improve TCR affinity.

The examples describe the generation and characterization of a single chain TCR that recognizes amino acids 59-67 of the vpr protein (AL9 epitope) in context with HLA-A2. The native TCR binds the AL9 consensus peptide with a $K_D$ of 1.8 µM, which is in the high affinity range of most TCRs. However it does not recognize some variants that are known to commonly arise during the course of infection, with good affinity. To overcome this limitation, and further increase its affinity, a mutant version of the protein was created by substitution of tyrosine (Y) to histidine (H) in the CDR3α loop region. The mutant binds with much higher affinity to the consensus AIIRILQQL (SEQ ID NO: 1) sequence, while retaining a high degree of peptide specificity. Importantly, variant epitopes which are known to frequently arise during HIV infection, could be recognized by the newly improved TCR with much higher affinity than the wild type TCR. Additionally, a multimeric form of the high affinity TCR could efficiently bind to CD4+ T cells infected with HIV-1. The AL9scTCR wild type and high affinity mutants were fused to the Ig heavy chain constant domain to deliver effector function. This fusion protein retains peptide specific binding activity, forms dimers and can mediate target cell killing by Fc-dependent cellular cytotoxicity.

CTLs specific to AL9 peptide (amino acids 59-67: AIIRILQQL (SEQ ID NO: 1)/HLA-A2 complexes were isolated from an HIV-1 infected patient, as described previously (Altfeld et al. 2005. J. Virol. 79: 5000) and served as the source for generating the TCR α and β cDNAs. The V regions of most frequently occurring TCR α and β chains obtained from these CTLs were TRAV5/TRAVJ36 and TRBV14/TRBJ2-1, respectively, as described previously (U.S. Ser. No. 11/784,277).

To generate high affinity TCRs, the TCR CDR regions and neighboring amino acid residues can be mutated and the resulting proteins screened. For the HLA-A2/AL9-specific TCR (AL9 TCR), the Vα and Vβ CDR sequences are shown in FIG. 1A with the corresponding nucleic acid coding regions shown in FIG. 2A. For this example, Vα CDR3 regions were mutated using a mutagenesis strategy where each of the amino acids in the CDR3 Vα region was systematically replaced by one of nine amino acids, chosen to represent the major side-chain chemistries provided by the 20 natural amino acids. Previous studies have shown that it is possible to generate high affinity TCRs by mutating the amino acids in the CDR3α loop (Holler et al. 2000 PNAS 10: 5387), which lie at the center of the peptide-MHC interface. Hence the gene sequence of AL9 TCR encoding 5 amino acids (Y-Q-T-G-A (SEQ ID NO: 2)) in the CDR3 Vα loop were mutated to the 9 amino acids representative of the major side chain chemistries. These amino acids were located between aa 93-97 of the TCR Vα chain, with changes at position 93 (tyr) showing improved (higher) affinity for HLA-A2/AL9 complex.

In the isolated Vα gene segment, a non-consensus serine codon was found at the position aa 39 in the second framework region. This codon was mutated to a consensus proline codon to assess the effects of this change on TCR productivity, stability and affinity.

To introduce sequences encoding different mutations in the Vα gene, the CDR3α sequence was modified by site-directed mutagenesis to contain a unique restriction enzyme site (AgeI). This change did not result in a change in the encoded amino acids. The mutated gene TCR Vα gene fragments were then generated by standard PCR methods using oligonucleotide primers encoding the desired sequence changes. These gene fragments were then cloned into the Vα gene replacing the wild-type sequence. The TCR α and β chains were cloned in the single-chain (sc) TCR format composed of a Vα domain linked to Vβ/Cβ domains via a flexible linker (Card et al. 2004 Cancer Immunol Immunother. 53:345; Mosquera et al. 2005 J. Immunol. 174:4781; Zhu X et al. 2006 J. Immunol. 176:3223). The Cβ domain was truncated just prior to the final cysteine.

To create the scTCR-birA fusion, the scTCR gene segment was cloned upstream of sequence encoding the birA tag sequence. The birA tag allows site-specific biotinylation of the protein for subsequent multimerization using strepta-vidin. To generate the scTCR IgG1 fusion, the scTCR gene segment was cloned upstream sequence encoding the human IgG1 constant chain region. Similarly scTCR-IL2, scTCR-INFα, scTCR-GMCSF, scTCR-IL15 and scTCR-IL15R fusions were generated by linking the scTCR gene segments with the appropriate cytokine or cytokine receptor gene sequences. For membrane expression, the scTCR gene was cloned upstream sequence encoding the HLA A2 transmembrane domain or the CD3zeta transmembrane domain. For membrane expression and intracellular signaling, the scTCR gene segments can be linked to sequences encoding CD3zeta, CD28, CD8, 4-1BB, Ox-40, ICOS and/or Lck domains. Alternatively, the TCR can be expressed on the cell surface as a heterodimeric α/β TCR containing TCR transmembrane and cytoplasmic signaling domains. Various soluble and membrane bound fusion proteins have been disclosed previously (Card et al. 2004 Cancer Immunol Immunother. 53:345; Mosquera et al. 2005 J. Immunol. 174:4781; Zhu X et al. 2006 J. Immunol. 176:3223; Belmont et al. 2006 Clin. Immunol. 121:29; Finney et al. 2004. J. Immunol. 172: 104; Brentjens et al. 2007 Clin Cancer Res. 13, 5426; Zhang et al. 2004. Cancer Gene Therapy 11, 487). Additional peptide linkers can be positioned between the scTCR and fusion protein domains and/or between different fusion protein domains to provide of optimal production, solubility, biological activity, protein-protein interactions, multimerization or positioning of the respective domains to avoid steric interference.

The scTCR fusion constructs were cloned into an expression vector downstream of a leader sequence to allow soluble or cell membrane expression. The vector contains promoter/enhancer regulatory sequences and poly A sequences to allow proper gene expression and genes encoding selectable markers to allow isolation of host cells containing the expression vector.

The AL9scTCR wild type (non-mutated) protein sequence, referred to as wild type or "wt", is shown in FIG. 1A. The AL9scTCR protein sequence containing a Tyr to His mutation at position 93 of the TCR Vα chain, referred to as single mutant or "sm", is shown in FIG. 1B. The AL9scTCR protein sequence containing a Tyr to His mutation at position 93 and a Ser to Pro mutation at position 39 of the TCR Vα chain, referred to as double mutant or "dm", is shown in FIG. 1C. Corresponding AL9scTCR wt, sm and dm nucleic acids sequences are shown in FIG. 2A-C. The protein sequences for leader sequence, various soluble fusion protein domains and linker sequences are shown in FIG. 3A-C with corresponding nucleic acid sequences shown in FIG. 4A-C.

Example 2

Protein Production and Purification

For production of the fusion proteins in mammalian cells, HEK-294 or CHO cells were transfected with the expression vectors using lipofectamine 2000. Single cell clones were selected by limiting dilution cloning, in medium containing G418 (2 mg/ml).

The AL9scTCR-birA wild type and mutant fusion proteins were purified from cell culture supernatants by immunoaffinity chromatography, using the anti-human TCR antibody Cβ mAb (BF1) 8A3.31, coupled to a Sepharose 4 Fast Flow column (Amersham Biosciences). The purified fusion proteins were biotinylated with biotin-protein ligase (Avidity) in the presence of excess biotin, according to the manufacturer's instructions to create monomers AL9sm/birA. The biotinylated AL9scTCR birA protein was multimerized with R-PE-conjugated streptavidin (Jackson Immunoresearch) at a TCR/streptavidin molar ratio of 4:1 for at least 60 min at 4° C.

The purified AL9scTCR-birA wild type and mutant fusion proteins were analyzed SDS-PAGE and stained with Coomassie G-250. The SDS gel analysis of the proteins under reducing and non-reducing conditions showed that the proteins were monomeric and had an approximate molecular weight of 52 kD. This is larger than the calculated molecular weight of 44.3 kD, suggesting that these proteins are glycosylated.

The AL9scTCR birA fusion proteins were biotinylated using biotin protein ligase. The efficiency with which the wild type and mutant proteins were biotinylated was compared in an ELISA using the BF1 antibody for capture and SA-HRP for detection. The results showed that both the proteins were biotinylated to a similar extent.

The AL9scTCR-IgG1 fusions are comprised of TCRs directly linked to the constant domain of the human IgG1 chain. The cysteine residues in the IgG hinge region are intact, allowing dimer formation, which is observed when the proteins are analyzed on non-reducing SDS-PAGE.

Example 3

Characterization of AL9scTCR Mutant Fusion Proteins by Concentration and Peptide-MHC-Binding Activity ELISAs The AL9scTCR wild type and mutant fusions produced in short-term cell cultures were assessed for TCR protein concentration and binding activity to peptide-MHC tetramers by ELISAs. In these assays, 96-well Maxisorb plates (Nunc, Rochester, N.Y.) were coated with the BF1 mAb (1 µg/ml). Cell culture supernatants containing the fusion proteins were added to blocked plates and incubated for 2 h at room temperature. After washing, the proteins were detected using AL9 peptide-HLA-A2 tetramer-HRP (0.5 µg/ml) for binding activity or the biotinylated anti-human TCR Cβ antibody mAb W4F (0.5 µg/ml) followed by streptavidin-HRP (0.5 µg/ml) for TCR protein concentration. The ABTS substrate was then added and absorbance was measured at 405 nm using a 96-well plate reader (Bio-Tek Instruments).

Figure 6:
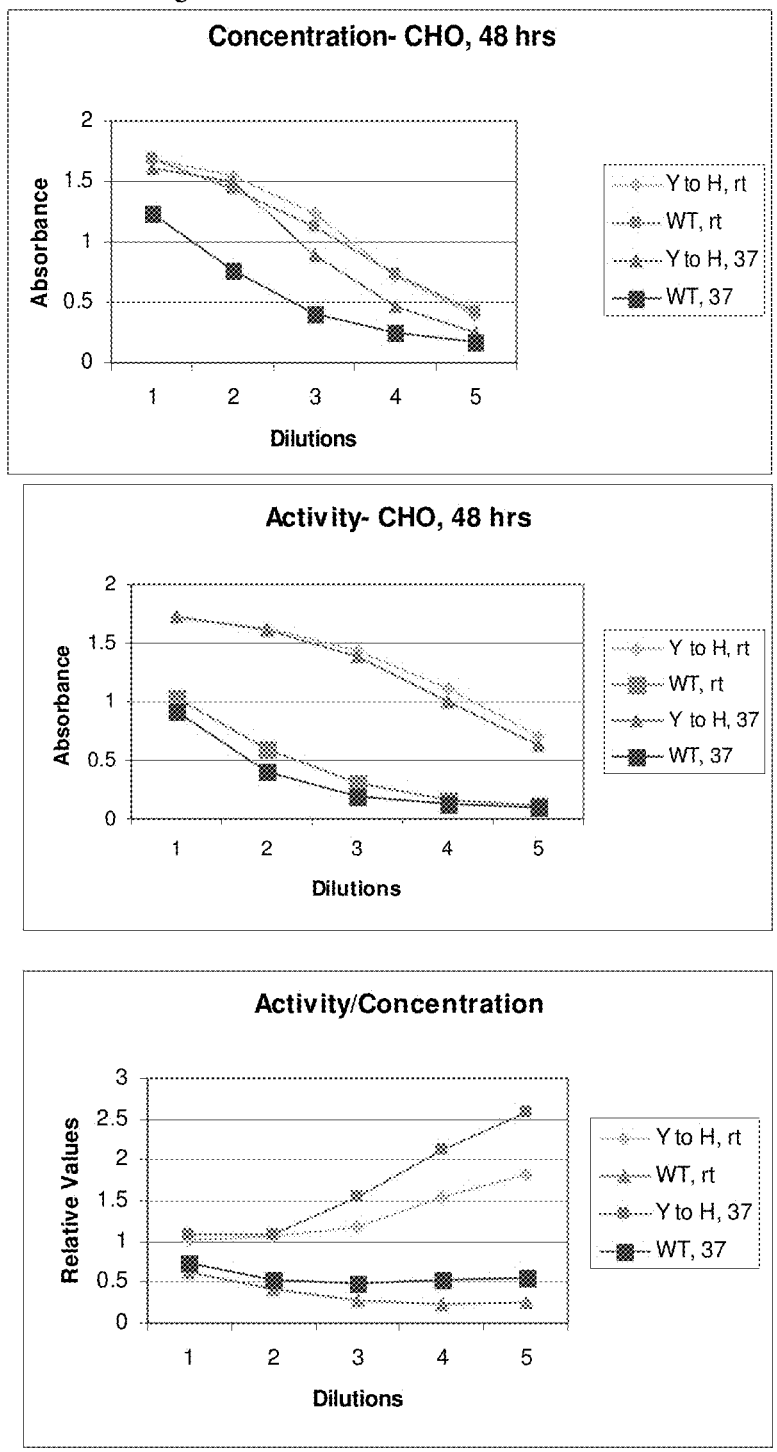
FIG. 6 is a characterization of Y93H AL9scTCR sm produced in CHO cells.

Various mutations at positions 93 and 97 of the TCR Vα chain were characterized in these assays as shown in FIG. 5. A majority of mutations at position 93 resulted in higher levels of protein in the short-term cell cultures, indicating higher expression levels and/or increased protein stability. Additionally several of the mutations also resulted in increased binding to AL9 peptide-HLA-A2 tetramer, indicating enhanced binding activity. In contrast, changes at position 97 (FIG. 5) or other positions in either the CDR3α or CDR3β regions failed to improve binding activity. When binding activity was normalized to protein levels, mutations at Y93 to L, K, Q or H showed significantly higher levels of AL9-HLA-A2 binding activity compared to the AL9scTCR wt protein. The Y93 to H substitution in the CDR3α loop yielded a TCR that had the best affinity compared to the wild type TCR and was further characterized. Previous studies showed that AL9scTCR wt protein was sensitive to temperature such that the protein was not observed at high levels in media following production in 37° C. cell culture conditions. Levels of the sm (Y93H) and wt AL9scTCR proteins produced by transfected CHO cells was examined in short-term cultures maintained at room temperature or 37° C. As shown in FIG. 6, the sm AL9scTCR exhibited much higher levels of expressed protein in 37° C. CHO cultures than the wt AL9scTCR protein, indicating improved production and/or protein stability. Again the sm AL9scTCR sm showed better binding to AL9-HLA-A2 complex than the AL9scTCR wt protein and when normalized to protein levels, indicating the Y93H AL9scTCR sm protein produced at either room temperature or 37° C. showed higher binding activity than the wt protein.

Figure 7:
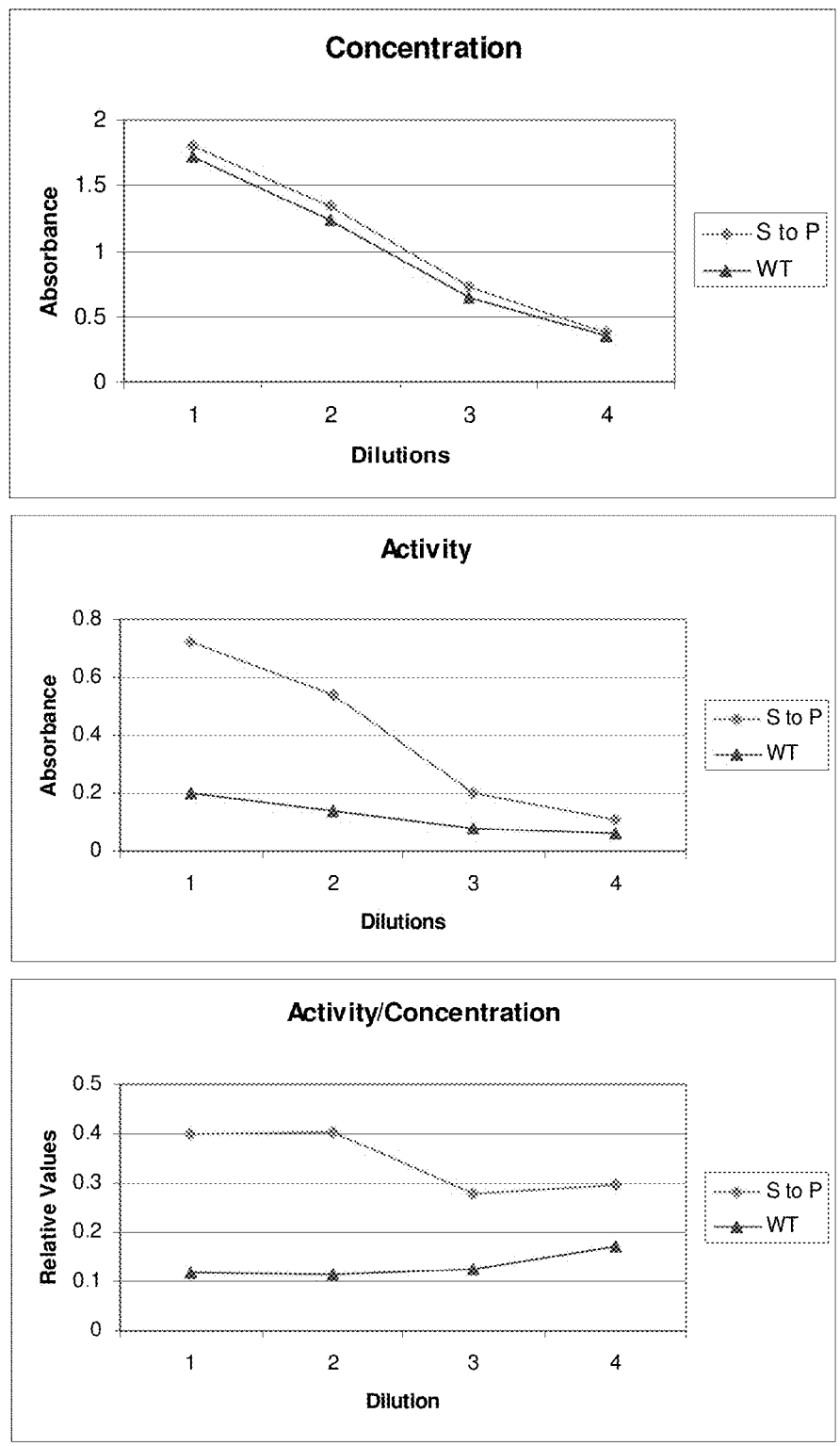
FIG. 7 is a characterization of S39P AL9scTCR produced in CHO cells.
Figure 8:
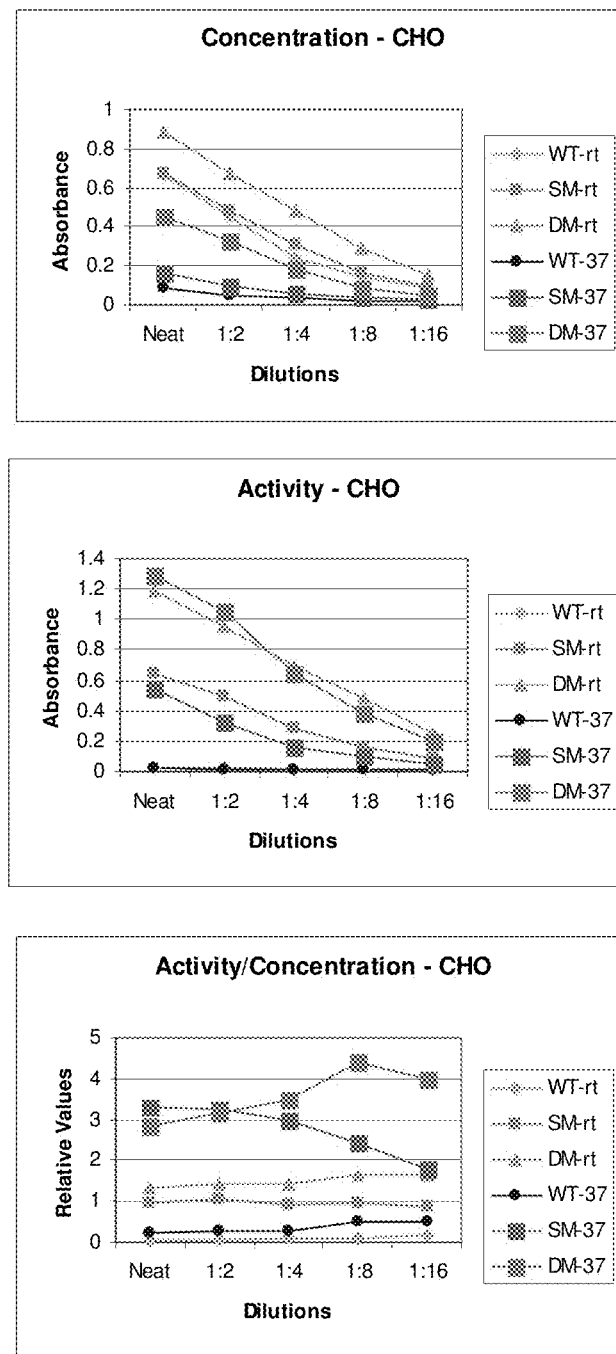
FIG. 8 is a characterization of AL9scTCR sm and dm produced in CHO cells.

Similar methods were used to characterize the S39P mutation in the TCR Vα chain. As shown in FIG. 7, AL9scTCR S39P expressed by transfected CHO cells in short term cultures exhibited increased binding activity to AL9-HLA-A2 complex than the AL9scTCR wt protein. When the S39P and Y93H mutations were combined into a single AL9scTCR, the resulting double mutant exhibited better productivity, stability at 37° C. and binding activity to AL9-HLA-A2 complex than the single mutant or wt AL9scTCR proteins (FIG. 8). Similar results were observed with proteins purified from CHO supernatants by BF1 mAb affinity chromatography. Both the AL9scTCR sm and dm constructs showed better stability at 37° C. and increased binding activity to AL9-HLA-A2 complex than the AL9scTCR wt protein (FIG. 9).

Example 4

Characterization of AL9scTCR Mutant Fusion Proteins by Flow Cytometry

Figure 10A:
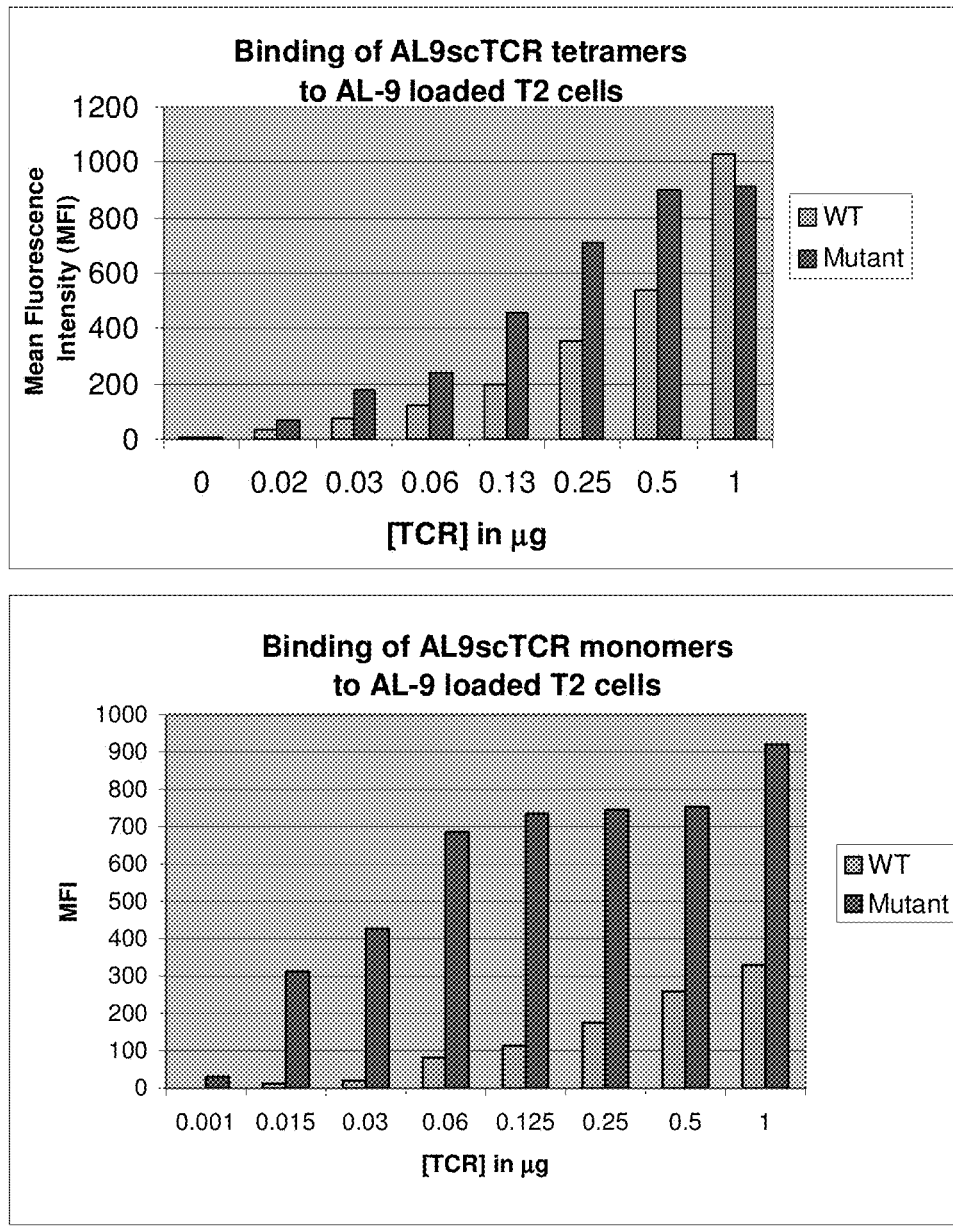
FIG. 10A depicts a titration of AL9scTCR wt and sm proteins to AL9-loaded T2 cells by flow cytometry.

Functional binding of AL9scTCR wt and mutant fusion proteins to AL9 peptide loaded HLA-A2-positive antigen presenting cells (T2 cells) was measured by flow cytometry. T2 cells were loaded with 50 µM of the consensus AL9 peptide for 3 hrs, at 37° C. The biotinylated AL9scTCR-birA proteins that had been multimerized by the addition of SA-PE were added at different concentrations from 1 to 0.001 µg for 30 min at 4° C. Following a wash step, the samples were analyzed on a FACS scan flow cytometer using CellQuest software (BD Biosciences). As shown in FIG. 10A, sm AL9scTCR-birA multimers showed 2-3 fold higher binding activity to the AL9 peptide loaded cells than the wt AL9scTCR-birA multimers when the TCR concentration was <0.5 µg/test.

Figure 10B:
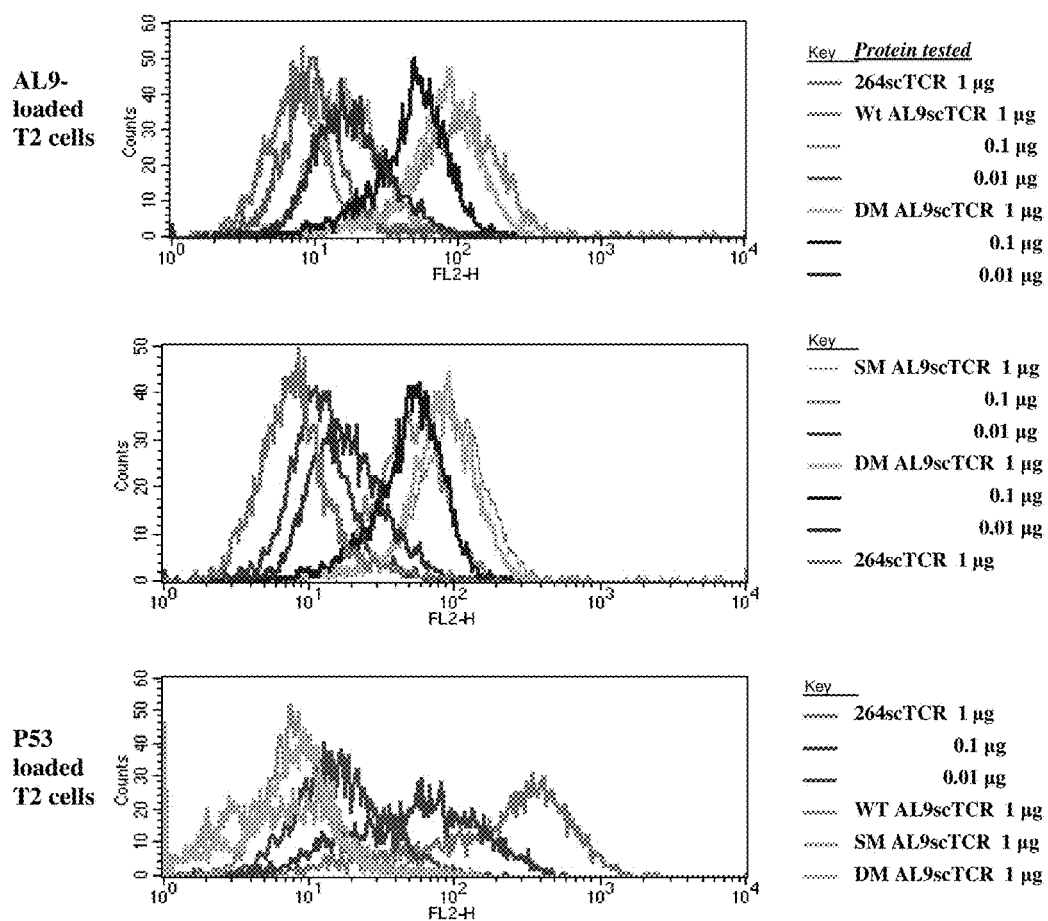
FIG. 10B depicts the binding of wt, sm and dm AL9scTCR multimers to T2 cells loaded with AL9 or p53 (control) peptide.

The monomeric forms of the wt and sm AL9scTCR-birA fusions were also used to detect peptide-MHC on the surface of target cells, in the same experiment. T2 cells were loaded with 50 µM AL9 peptide as described above. Biotinylated forms of AL9 wt and AL9sm TCRs were added at equivalent molar amounts as with the multimeric forms ranging from 1 to 0.001 µg. Following a wash step the bound monomers were detected with SA-PE. There was a 2-3 fold higher binding of the AL9scTCR sm monomer compared to the wild type monomer at 0.5-1 µg. This difference was increased to 4-8 fold at concentrations from 0.25 to 0.06 µg and 20-30 fold at concentrations from 0.03 to 0.001 µg. Thus the difference between the wild type and sm AL9scTCR was particularly evident when the monomeric form of the scTCR was used (FIG. 10A). There was little or no binding of either the wild type or mutant TCR monomers or tetramers to unpulsed cells even at the highest concentration. Similar studies conducted with the dm AL9scTCR-birA fusion showed that this protein also exhibited increased binding activity to AL9 peptide loaded T2 cells compared to the wt AL9scTCR (FIG. 10B). Additionally both the sm and dm AL9scTCR-birA fusions were able to bind AL9 peptide presented by HLA-A2+ B cells (FIG. 10C). In these studies the 264scTCR and p53 aa264-272 peptide were used as negative control reagents to assess TCR and peptide specificity and expected specificities were observed. Together these data confirm that the AL9scTCRs are biologically functional in the three-domain single chain format and that the AL9scTCR sm and dm fusion specifically binds to AL9 peptide loaded cells with higher affinity than the wild type AL9scTCR.

Specific interaction between the wild type or sm AL9scTCR birA proteins and cognate peptide-MHC was confirmed by analyzing their binding to a panel of irrelevant control peptides. T2 cells were loaded with the consensus AL9 peptide or peptides from HIV-1 gag (77-85), pol (464-472), CMV, HCV core, HBV env, p53 (264-272), MART-1 or were left unpulsed. Biotinylated wild type AL9scTCR, sm AL9scTCR or control MART1scTCR were then added, followed by incubation with streptavidin-PE. No binding of either the wild type or sm AL9scTCRs to any irrelevant peptides was observed (FIG. 10D). Thus the higher affinity of the sm AL9scTCR does not compromise its peptide binding specificity.

Figure 11:
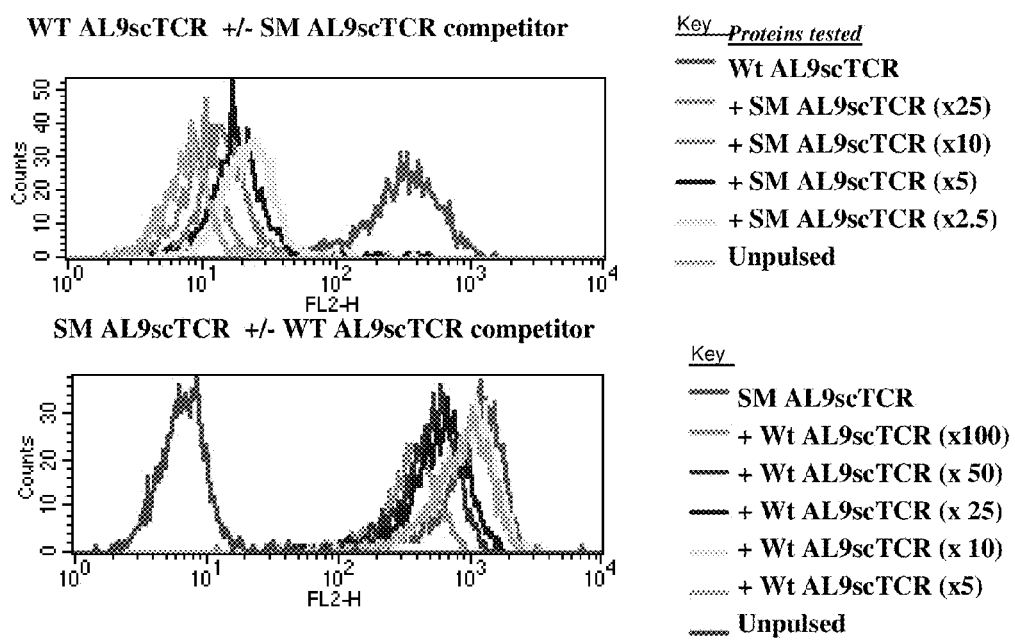
FIG. 11 depicts the competitive binding analysis by flow cytometry.

The ability of the wild type or sm AL9scTCR-birA fusion proteins to compete with each other for binding to AL9 peptide loaded T2 cells was analyzed. The binding of the biotinylated wild type or sm AL9scTCR was determined in the presence or absence of 2-100 fold excess of non-biotinylated competitor. The high affinity single mutant could compete with the wild type AL9scTCR very efficiently even at 2 fold excess, as shown in FIG. 11. Higher concentrations of 5-10 fold excess were only slightly better and there was almost complete abrogation of binding of the wt AL9scTCR with 25 fold excess of the mutant. In contrast, the wild type AL9scTCR could not compete efficiently with the sm AL9scTCR. With a 10 fold excess or less of the wild type there was little or no inhibition. At a 25-100 fold excess, some inhibition is observed, but it was not very significant. Thus the wild type AL9scTCR cannot efficiently block binding of the sm AL9scTCR even at high concentrations, but the mutant is a very good competitor of the wt AL9scTCR even at a 2 fold excess. These data support the conclusion that the sm AL9scTCR has higher binding activity to AL9-HLA-A2 complex and can inhibit binding of the wt AL9 TCR.

Figure 12:
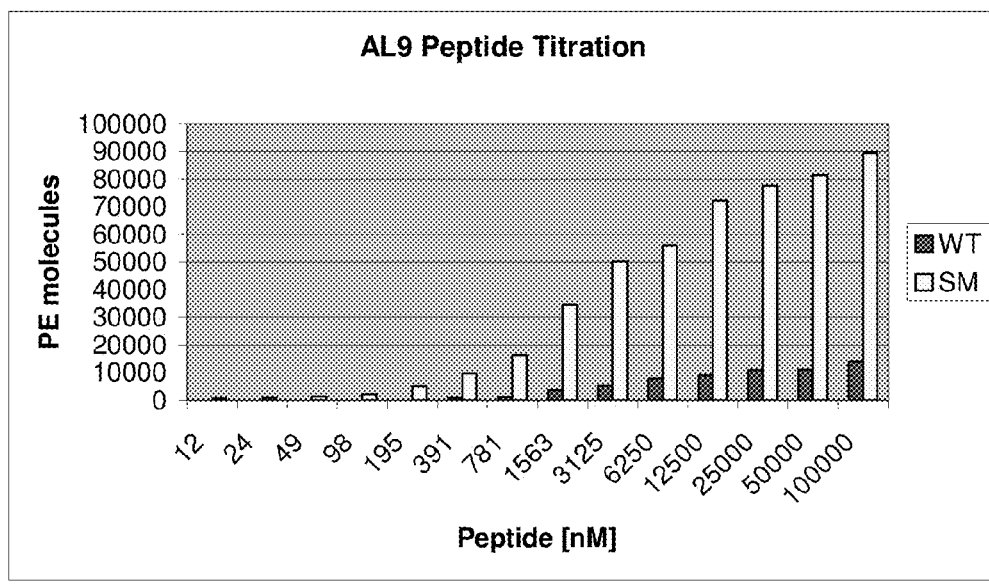
FIG. 12 depicts the binding of wt and sm AL9scTCR monomers to T2 cells loaded with different amounts of AL9 peptide.

The sensitivity of the wt and sm AL9scTCR-birA fusions was evaluated by comparing their ability to detect varying amounts of peptide on the cell surface. T2 cells were loaded with AL9 peptide at concentrations ranging from 12 nM to 100 µM. 0.5 µg of monomeric wt or sm AL9scTCR-birA were then added and binding was evaluated by flow cytometry. To estimate the number of PE molecules bound per cell, the mean fluorescent intensity obtained at various concentrations of peptide was compared to a standard curve of PE-coupled calibration beads, which have known amounts of PE per bead. As shown in FIG. 12, there is a significant increase in the ability of the sm AL9scTCR compared to wt AL9scTCR to detect AL9 peptide loaded T2 cells, at all the peptide concentrations tested. The sm AL9scTCR was able to stain T2 loaded cells with as little as 12 nM AL9 peptide whereas the wild type TCR could only detect 195 nM peptide on the surface of T2 cells. Similar results were observed with the dm AL9scTCR fusion.

Example 5

Characterization of AL9scTCR Mutant Fusion Proteins Binding to AL9 Peptide Variants Crystal structures of TCR-peptide/HLA-A2 complexes have suggested that amino acids in the middle of a 9-mer peptide make contacts with the CDR3 regions of the TCR. In order to determine which peptide amino acids are important in binding the wild type and mutant TCRs, alanine substitutions were made at positions 60, 62, 64, 65, 66 and 67 of the AL9 peptide (aa59-67: AIIRILQQL (SEQ ID NO: 1)). The relative binding (IC50) of these variants to HLA-A2 complex was assessed by competition analysis as described previously (Altfeld et al. 2005. J. Virol. 79: 5000) and is indicated for each peptide in FIG. 13. These peptides were loaded on T2 cells and the cells were stained with the wt and sm AL9scTCR-birA multimers as described above. Flow cytometric analysis was performed to evaluate the relative binding affinity of wt and sm AL9scTCR multimers for the consensus peptide and variant peptide loaded cells. The 264scTCR multimer served as a control reagent.

The results showed that replacement of amino acids at positions 60, 65, 66 and 67 did not result in any significant differences in the binding between the wt and sm AL9scTCRs (FIG. 13). However, substitution of the Leu at position 64 with Ala significantly diminished the binding of the wild type, but not the sm AL9scTCR. This suggests that position 64 may be a crucial contact for the native TCR, but not for the high affinity mutant.

Replacement of the Arg at position 62 to Ala resulted in an insoluble peptide whereas a Glu substitution at this position was soluble. This substitution completely abolished binding of both the wt and sm AL9scTCR multimers both in the monomer and tetramer formats, suggesting that this is a critical contact for both the wild type and mutant TCR-peptide interaction.

Different naturally occurring variants of the AL9 epitope in HIV have been reported in the Los Alamos database (http://www.hiv.lanl.gov). Analysis of the most frequently occurring variants, shows isoleucine to leucine variants at position 60 and threonine and methionine substitutions at positions 61 and 63 (FIG. 14A, Altfeld et al. 2005. J. Virol. 79: 5000). Peptides corresponding to these and other variants were synthesized and the binding of the wild type, sm or dm AL9scTCRs to variant peptide loaded cells was compared by flow cytometry in a series of studies shown in FIG. 14B. As above, T2 cells were loaded with AL9 consensus or variant peptides (50 µM each) for 3 hrs, at 37° C., and stained with the wt, sm or dm AL9scTCR multimers labeled with PE.

Figure 14C:
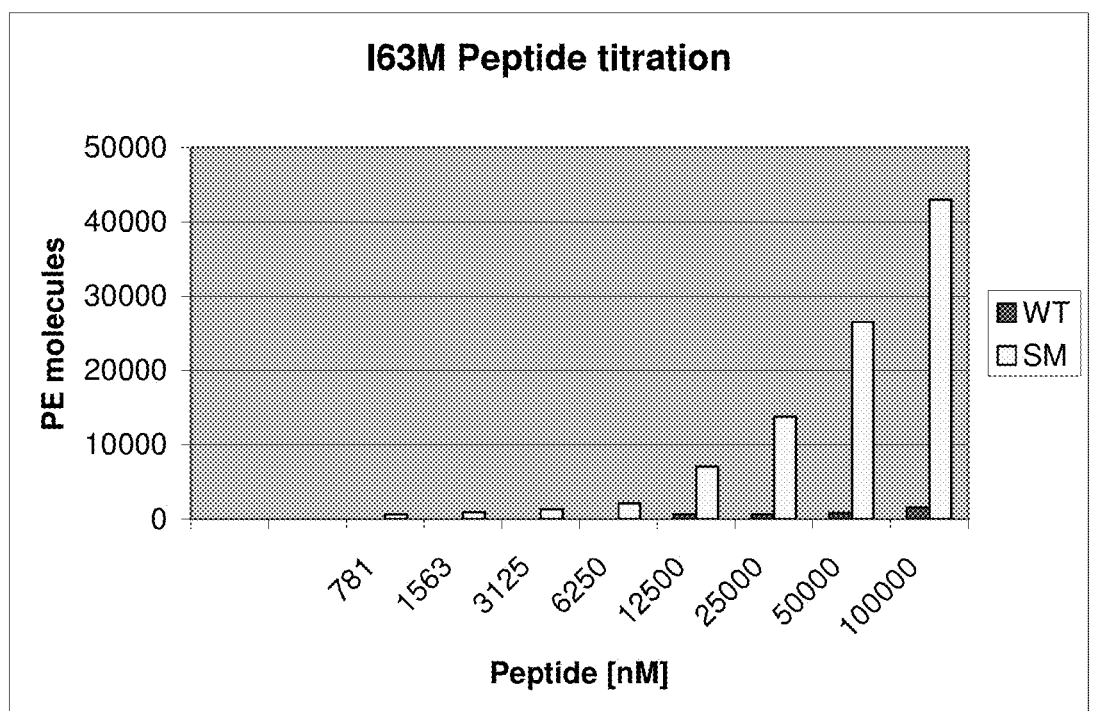
FIG. 14C depicts the AL9 I63M peptide titration.

The wt AL9scTCR multimer showed reduced binding to the AL9 variants with Thr and Met substitutions at position 63. In contrast the sm and dm AL9scTCR multimers exhibited good binding to these variants. Substitution of positions 60 and 61 in the AL9 peptide did not affect binding of either the wt or sm AL9scTCR. Titration of the I63M peptide at concentrations from 50 µM-0 nM confirmed that the sm AL9scTCR, but not the wild type TCR tetramer, could recognize this variant as shown in FIG. 14C.

Since substitution at position 62 to Glu had been shown to abrogate binding of both the wild type and mutant AL9scTCR, it was of interest to determine what effect replacement of Arg with Lys would have on the binding of these TCRs. This substitution has been reported as a naturally occurring variant of HIV in the database. A Lys substitution at position 62 significantly decreased binding of the wild type but not the high affinity sm AL9scTCR multimer (FIG. 14B).

Figure 14D:
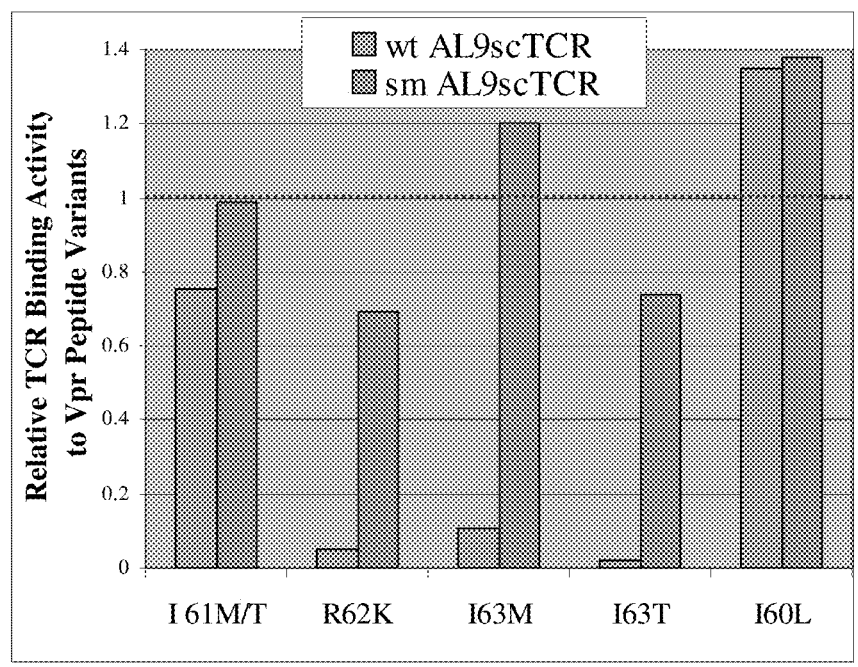
FIG. 14D depicts a summary of the relative binding of wt and sm AL9scTCR fusions to AL9 peptide variants compared to the AL9 consensus.

Thus the sm and dm AL9scTCRs not only binds the AL9 peptide consensus with higher affinity, these proteins can also recognize variants at position 62, 63 and 64 much better than the wild type AL9 TCR (FIG. 14B). FIG. 14D shows a summary of the relative binding activity of the wt and sm AL9scTCR multimers to common AL9 epitope variants relative to the AL9 consensus peptide. The sm AL9scTCR retains binding activity to these variants at >70% compared with that observed for the consensus peptide, indicating that this mutant TCR fusion protein should be able to recognize HIV-infected cells displaying these variant epitopes.

Example 6

Figure 15:
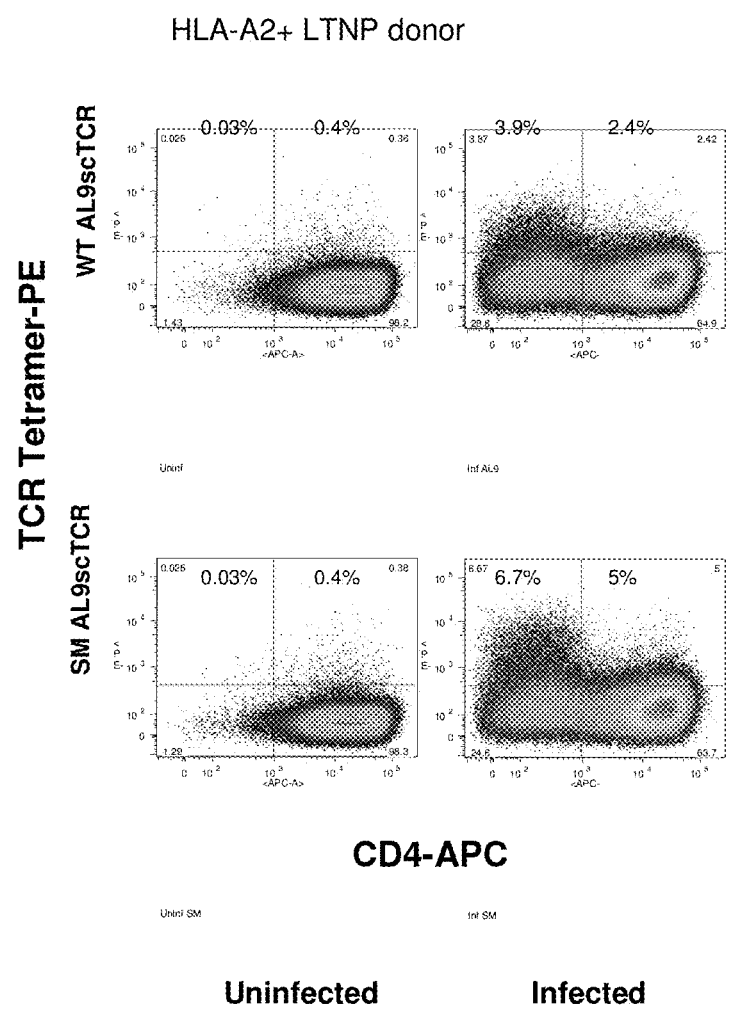
FIG. 15 depicts the binding of wt and sm AL9scTCR multimers to AL9 peptide presented by HIV infected human CD4 T cells.

Detection of AL9 Antigen Presentation on HIV-Infected Human T-Cells by AL9scTCR Fusion Proteins The results shown above demonstrate that the wt and mutant AL9scTCR proteins were capable of binding AL9 peptide-HLA-A2 complex and endogenously added AL9 peptide presented on HLA-A2+ cells. However, in order to target HIV-infected cells, the TCR fusion proteins must be sensitive and specific enough to detect AL9 presented on the cell surface that is generated via the antigen presenting pathway for internally expressed HIV vpr protein. To examine this, CD4+ T cells from HLA-A*0201 donors were isolated by magnetic beads (Miltenyi Biotech) and were stimulated with media containing ant-CD3 (OKT3; Coulter), anti-CD28 (PharMingen), and IL-2 as described previously (Migueles et al. 2002 Nat Immunol 3: 1061). On day 3, $5 \times 10^6$ cells were infected with 5,000 $TCID_{50}$ of $HIVSF_{162}$ in 200 µl of media for 1 h at 37 C and then were maintained in culture at $10^6$ cells/ml in 24-well plates for 6 days further. On day 6, CD8+ cells were depleted by using magnetic beads. The percent of infected cells was documented by intracellular staining for p24 with Kc57-FITC or Kc57-RD1 (Coulter). The infected cells then were stained with wt and sm AL9scTCR multimers and anti-CD4 mAb-APC. HIV infections results in down regulation of cell surface expression of CD4. Thus AL9 peptide presentation can be assessed in infected cells with low levels of CD4 staining. As shown in FIG. 15, wt and sm AL9scTCR-birA multimers were capable of detecting AL9 peptide presented by HIV infected T cells. There was a 15-fold increase in the percentage of wt AL9scTCR-positively staining cells and a 27-fold increase in percentage of sm AL9scTCR-positively staining cells when comparing infected cells to uninfected cells. Additionally increased AL9scTCR staining was observed in cells that have down-regulated CD4. In this study the sm AL9scTCR-birA multimer detected about 2-fold more HIV-infected cells than the wt AL9scTCR-birA multimer, consistent with the increased binding activity of the TCR mutant for the AL9 peptide.

Example 7

Figure 16A:
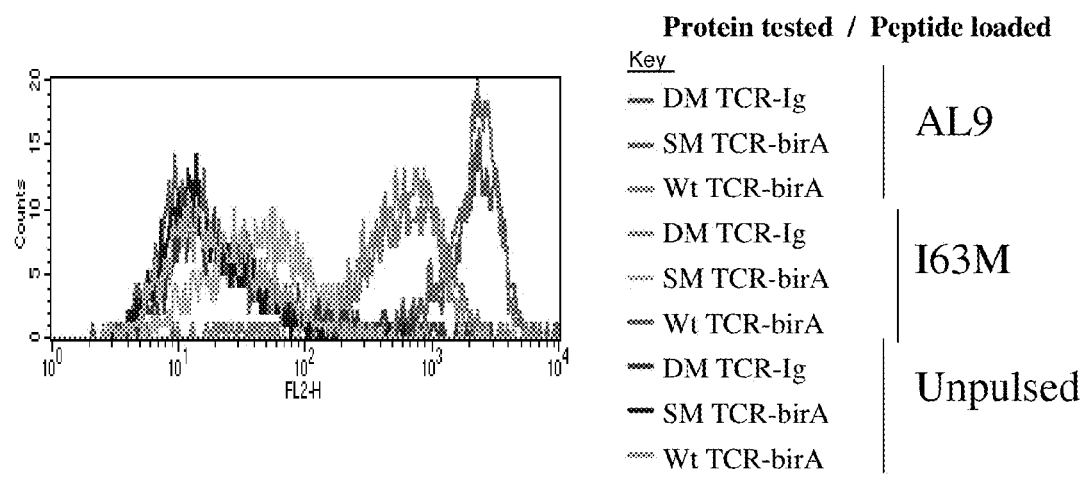
FIG. 16A depicts DM AL9scTCR-Ig fusion protein binds AL9 and AL9 variants.
Figure 16B:
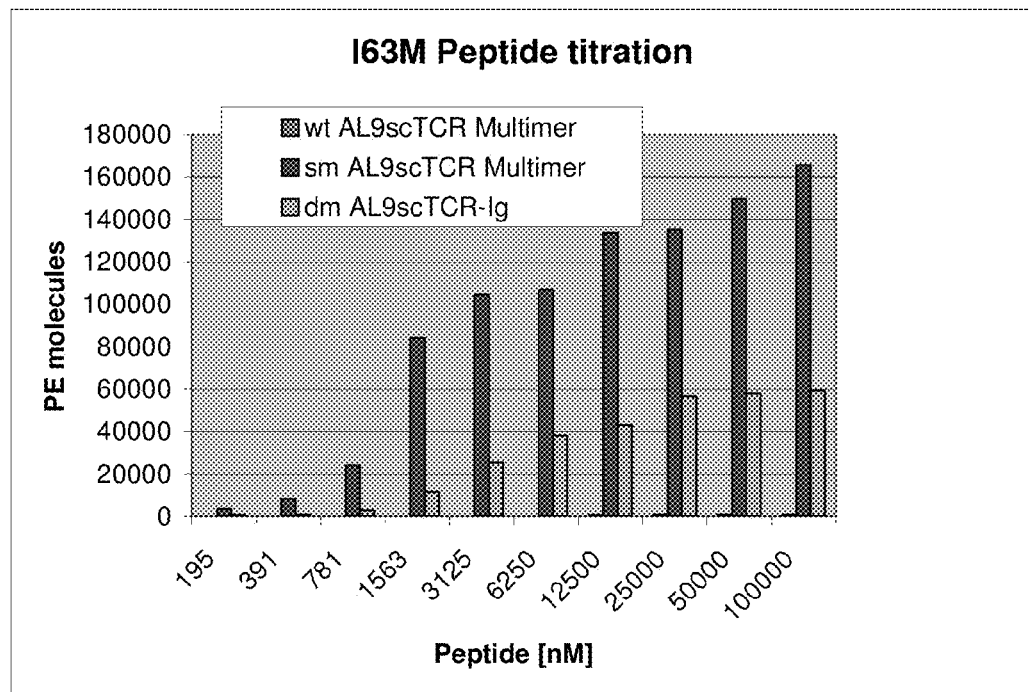
FIG. 16B depicts DM AL9scTCR-Ig fusion protein binding to AL9 I63M variant
Figure 16C:
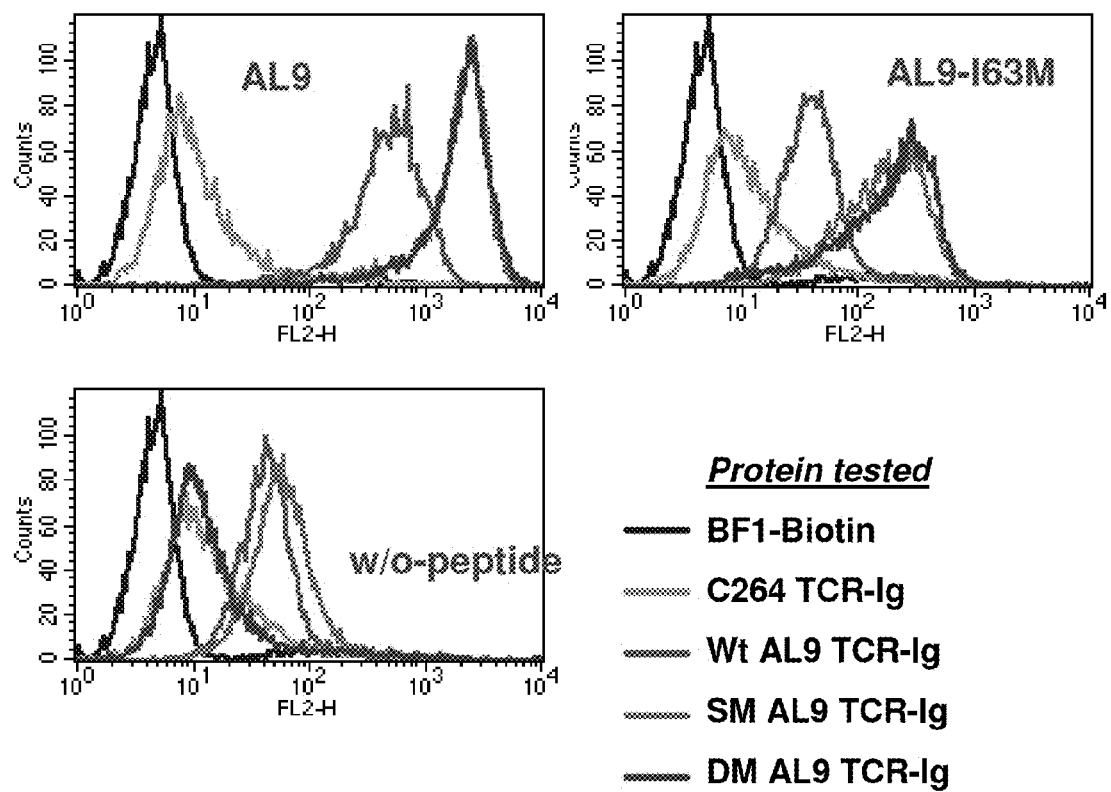
FIG. 16C depicts WT, SM and DM AL9scTCR-Ig fusion protein binds AL9 and AL9 variants

Characterization of AL9scTCR-Ig Fusion Proteins Binding to AL9 Peptide and Peptide Variants As indicated above, AL9scTCR-Ig fusion proteins were produced and purified. The binding activity of the dm AL9scTCR-Ig fusion was compared to wt and sm AL9scTCR-birA fusions using AL9-loaded T2 cells. In this assay TCR binding was detected using a biotinylated BF1 mAb followed by SA-PE. As shown in FIG. 16A, the dm AL9scTCR-Ig fusion protein exhibited good binding to T2 cells loaded with either the AL9 consensus peptide or the AL9 I63M variant. In fact the dimeric dm AL9scTCR-Ig shows better binding to the AL9 I63M variant than the monomeric sm AL9scTCR-birA fusion. The binding activity of the dm and sm AL9scTCR-Ig fusions was compared to the wt AL9scTCR-birA multimers and wt AL9scTCR-Ig fusions using T2 cells loaded with the AL9 consensus and AL9 I63M variant (FIG. 16B-C). These studies verified that the dm and sm AL9scTCR-Ig fusions exhibited better binding to the AL9 and AL9 variants than the wt AL9scTCR protein. Interestingly the dm AL9scTCR-Ig fusion protein shows less background binding to unpulsed T2 cells than either the wt or sm AL9scTCR-Ig fusions (FIG. 16C). The higher background staining of the wt or sm AL9scTCR-Ig fusion is likely due to binding of the Ig Fc domain to receptors on T2 cells. The difference in background binding between the dm and sm AL9scTCR proteins was not observed with the birA fusion multimer format, suggesting that the TCRα FR2 mutation in the double mutant in the Ig format results in less non-specific binding activity. This effect is advantageous for targeting specific biological activity.

Example 8

AL9scTCR-Ig Fusion Proteins Mediate AL9 Peptide Specific Cytotoxic Activity

The ability of the wt, dm and sm AL9scTCR-Ig fusions to direct Fc-dependent cellular cytotoxicity against AL9 loaded targeted cells was examined. In these assays the AL9scTCR-Ig fusions act to conjugate the Fc receptor-bearing immune effector cells and the peptide-MHC presenting target cells and the effector cells mediate target cell lysis through an ADCC-like mechanism. Human PBMCs, which serve as immune effector cells in this example, were isolated from human blood buffy coats by gradient centrifugation through HistoPague (Sigma-Aldrich). T2 cells pulsed with peptide at 50 µg/ml at 37° C. for 2 hours were used as target cells. The target cells are labeled with Calcein-AM at 50 µg/ml at 37° C. for 1 hours and washed two times and added into 96-U-plate at 20000/well in RPMI-10 media. The dm, sm and wt AL9scTCR-Ig was added to the wells at different concentration. The effector cells were then added (100:1 E:T ratio) and the culture incubate at 37° C. for 2 hours. The fluorescent intensity (FI) of the Calcein released into the supernatant by cell lysis was measured with a fluorescent plate reader (excitation wavelength=485 nm; emission wavelength=538 nm; cutoff=530 nm). The specific cytotoxicity was calculated using the following formula: percentage of cytotoxicity=(FI of test sample−FI of target cells with medium)÷(FI of target cells treated with 0.04% Triton X-100−FI of target cells with medium)×100.

Figure 17A:
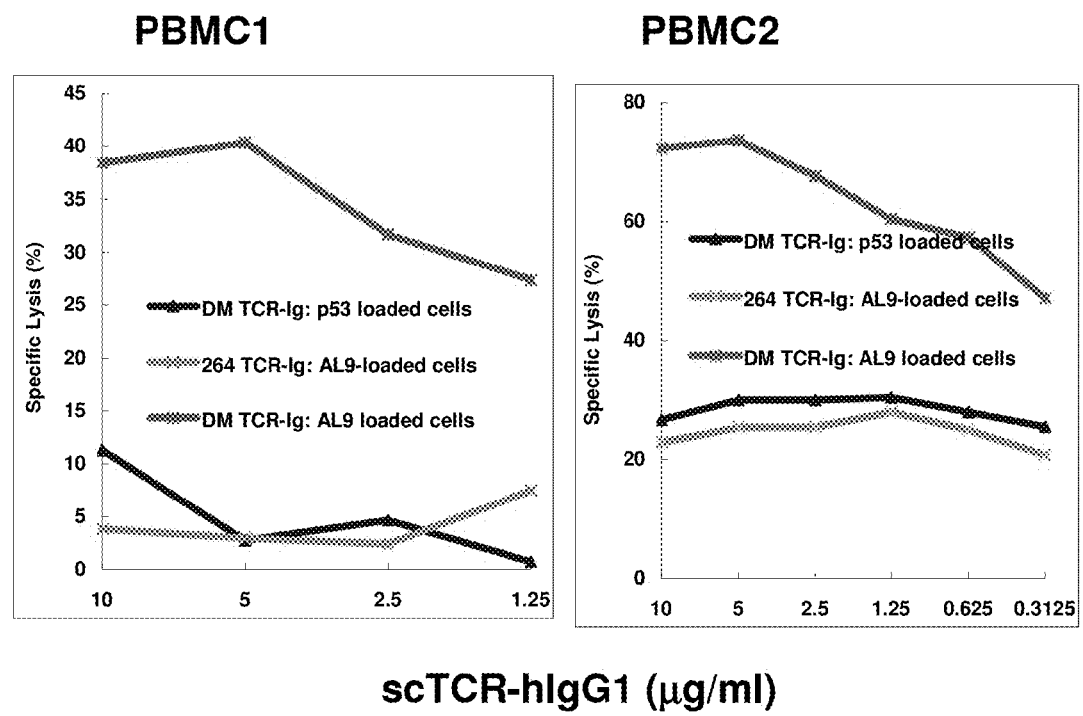
FIG. 17A depicts DM AL9scTCR-Ig fusion protein mediates cytolytic activity against AL9-loaded T2 cells
Figure 17B:
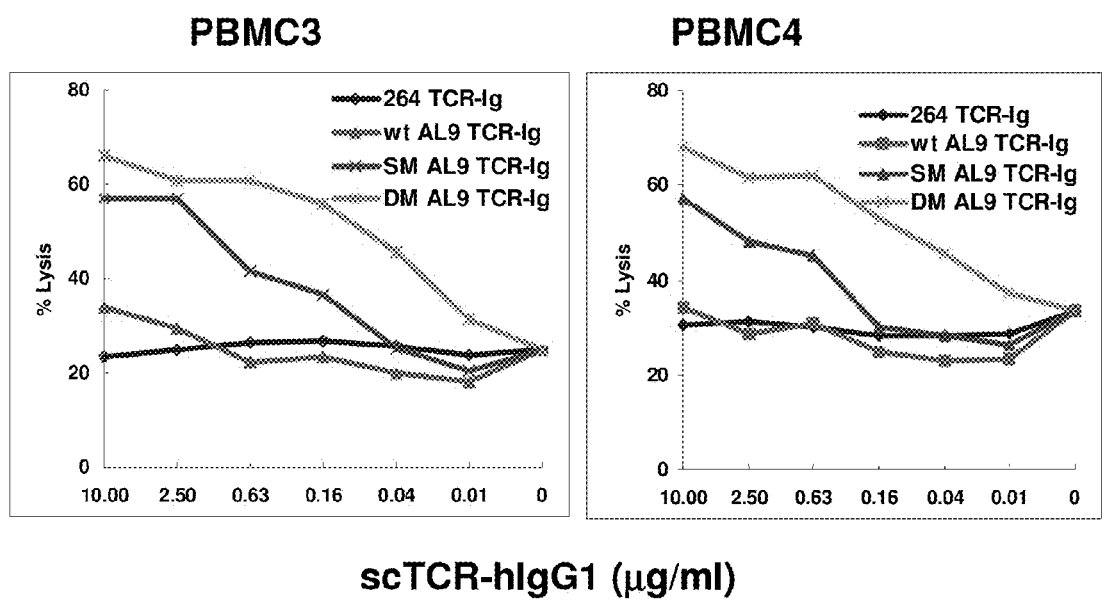
FIG. 17B depicts DM and SM AL9scTCR-Ig fusion proteins mediate cytolytic activity against AL9-loaded T2 cells.

As shown in FIG. 17A, the dm AL9scTCR-Ig fusion protein effectively directs human PBMC cytolytic activity against T2 cells pulsed with AL9 peptide but not T2 cells pulsed with p53 264-272 peptide. A control 264scTCR-Ig fusion protein did not show the same activity against the AL9-loaded T2 cells demonstrating the specificity of this assay. Similar results were seen with different preparations of PBMCs. FIG. 17B shows additional cytotoxicity assays comparing the activity of the dm, sm and wt AL9scTCR-Ig fusion proteins against AL9 loaded T2 cells. The results indicated that dm and sm AL9scTCR-Ig fusion were effective at mediating ADCC-like activity against AL9-loaded cells whereas the wt AL9scTCR-Ig fusion was not. These results indicate that AL9scTCR mutants confer increased cytolytic bioactivity against cells displaying the HIV AL9 epitope that was not observed with the wt AL9 TCR.

Similarly, the ability of the mutant AL9scTCR-Ig fusion proteins to direct immune effector cell cytolytic activity against HIV infected cells will be assess. HIV infected cells will be generated as described in Example 6 and will be used as target cells in the Calcein release assays as described above. A specific increase in the lysis of HIV-infected cells due to the presence of the mutant AL9scTCR-Ig fusion in the culture media would demonstrate that the mutant AL9scTCR-Ig fusion can act as a bridging molecule directing immune cytolytic activity against HIV infected cells.

Example 9

Mutant AL9scTCR Fusion Proteins Exhibit Increased Affinity to AL9/HLA-A2 Complexes The binding affinity parameters of AL9scTCR fusion protein:AL9/HLA-A2 complexes interactions were determined by surface plasmon resonance methods. Biotinylated AL9 or I63M pMHC complexes or irrelevant control pMHC complexes were bound to a streptavidin sensor chip surface. Soluble TCR-birA proteins were allowed to flow over the relevant cells and responses measuring protein-protein interactions were recorded in real time using BIAcore technology. Binding parameters were estimated using BIAevaluation software. The results of these analysis for AL9scTCR-birA fusion proteins are shown in Table 1 and for the AL9scTCR-Ig fusion proteins are shown in Table 2. The results clearly indicate that the sm AL9scTCR protein as a birA or Ig fusion has increase binding affinity to AL9/HLA-A2 and I63M AL9/HLA-A2 complexes. Additionally the dimeric sm AL9scTCR-Ig fusions display better binding to the AL9/HLA-A2 complexes than the monomeric sm AL9scTCR-birA molecules due to their increase avidity.

TABLE 1

Binding affinities for wt and sm AL9scTCR-birA fusion for AL9 peptide and I63M AL9 variants complexed to HLA-A2 molecules

| Constants | Wt AL9scTCR birA | sm AL9scTCR-birA |
|---|---|---|
| | AL9-HLA-A2 | |
| $K_D$ | 1.8 µM | 120 nM |
| $K_{on}$ (M$^{-1}$s$^{-1}$) | 9440 | 30200 |
| $K_{off}$ (s$^{-1}$) | 1.75 × 10$^{-2}$ | 3.6 × 10$^{-3}$ |
| | I$_{63}$M AL9-HLA-A2 | |
| $K_D$ | No binding | 6 µM |

TABLE 2

Binding affinities for wt and sm AL9scTCR-Ig fusion for AL9 peptide and I63M AL9 variants complexed to HLA-A2 molecules

| Constants | Wt AL9scTCR Ig | sm AL9scTCR Ig |
|---|---|---|
| | AL9-HLA-A2 | |
| $K_D$ | 83.4 nM | 58.9 nM |
| $K_{on}$ (M$^{-1}$s$^{-1}$) | 2.62 × 10$^4$ | 2.01 × 10$^4$ |
| $K_{off}$ (s$^{-1}$) | 2.18 × 10$^{-3}$ | 1.19 × 10$^{-3}$ |
| | I$_{63}$M AL9-HLA-A2 | |
| $K_D$ | No binding | 224 nM |
| $K_{on}$ (M$^{-1}$s$^{-1}$) | | 2.98 × 10$^4$ |
| $K_{off}$ (s$^{-1}$) | | 6.67 × 10$^{-3}$ |

Example 10

Gene Transfer and Cell-Based Approaches Using Mutant AL9 TCRs to Kill HIV Infected Cells The TCRs of the invention could be used in gene therapy or cell-based therapeutic approaches to kill HIV infected cells or prevent or treat HIV infection. For example, TCR genes encoding the mutant AL9 TCR and transmembrane and cytoplasmic signaling domains will be transferred into immune cells such that the immune cells now expressed the high affinity AL9 TCR on the cell surface. These cells will become activated to express immune functions when the AL9 TCR interacts with HIV vpr peptide displayed in the HLA-A2 complex. These cells will be used in killing HIV-infected cells ex vivo or, following infusion into patients with HIV infection, kill HIV infected cells in the patient. Alternatively, the TCR genes in the appropriate vectors will be directly administered to the patients, thereby allowing gene transfer into the patient's immune cells and expression of the high affinity AL9 TCR on the surface of these cells in vivo. Such cells could provide protective or therapeutic activity against HIV infection.

In one particular example, human PBMC will be isolated from an HIV-infected patient. TCR genes encoding the mutant AL9 TCR and transmembrane and cytoplasmic signaling domains will be transferred into these cells ex vivo allowing expression of the TCRs on the cell surface. The immune cells will be transferred back into the patient where they will mediate effector functions against HIV infected cells. The cytotoxic activity of the immune cells against HIV-infected cells will also be tested in vitro using the calcein release assays described above.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule encoding an isolated T cell receptor (TCR) that specifically binds an HIV Vpr epitope, wherein said HIV Vpr epitope comprises a peptide sequence selected from the group consisting of SEQ ID NO: 1 and SEQ ID NOs: 31-44, and wherein the isolated TCR comprises a Y93H or S39P mutation in the Vα chain of the polypeptide set forth in SEQ ID NO: 3.

2. The isolated nucleic acid molecule of claim 1, wherein the nucleic acid comprises the nucleic acid sequence set forth in SEQ ID NO: 7 or SEQ ID NO: 8.

3. An expression vector comprising the nucleic acid molecule of claim 1.

4. An isolated host cell comprising the expression vector of claim 3.

5. The host cell of claim 4, wherein the host cell is mammalian host cell.

6. The host cell of claim 5, wherein the mammalian cell is a human cell.

7. The host cell of claim 6, wherein the human cell is a peripheral blood mononuclear cell (PBMC).

8. The host cell of claim 4, wherein the host cell expresses an isolated TCR that specifically binds an HIV Vpr epitope, wherein said HIV Vpr epitope comprises a peptide sequence selected from the group consisting of SEQ ID NO: 1 and SEQ ID NOs: 31-44, and wherein the isolated T cell receptor comprises a Y93 H or S39P mutation in the TCR Va chain of the polypeptide set forth in SEQ ID NO: 3.

9. The isolated nucleic acid molecule of claim 1, wherein the mutation increases the productivity, stability, specific binding activity, or functional activity of the TCR.

10. The isolated nucleic acid molecule of claim 1, wherein the mutation reduces the non-specific binding of the TCR compared to the wild type TCR.

11. The isolated nucleic acid molecule of claim 1, wherein the TCR is a single-chain TCR.

12. The isolated nucleic acid molecule of claim 1, wherein the TCR is a heterodimeric TCR.

13. The isolated nucleic acid molecule of claim 1, wherein the TCR comprises more than one TCR binding domain.

14. The isolated nucleic acid molecule of claim 1, wherein said TCR comprises Y93H and S39P mutations.

15. The isolated nucleic acid molecule of claim 1, wherein the peptide is presented in the context of HLA-A2.

16. The isolated nucleic acid molecule of claim 1, wherein the HIV epitope is presented in the context of HLA-A2.

17. The isolated nucleic acid molecule of claim 1, wherein the TCR has greater stability at elevated temperatures than the wild type TCR.

18. The isolated nucleic acid molecule of claim 1, wherein the TCR is soluble.

19. The isolated nucleic acid molecule of claim 1, wherein the TCR further comprises a fusion to a functional polypeptide domain, diagnostic/imaging agent, drug-containing nanoparticle, therapeutic agent, cytotoxic agent or anti-viral agent.

20. The isolated nucleic acid molecule of claim 1, wherein the functional polypeptide domain comprises a cytokine, immunoglobulin domain, receptor domain or polypeptide tag sequence.

21. The isolated nucleic acid molecule of claim 20, wherein the cytokine comprises IL-2, IL-15, GM-CSF, or interferon, the immunoglobulin domain comprises IgG1 constant regions or Ig Fc domain, or a fragment thereof.

22. The isolated nucleic acid molecule of claim 20, wherein the polypeptide tag comprises the BirA sequence.

23. The isolated nucleic acid molecule of claim 1, wherein the TCR further comprises a transmembrane domain allowing cell surface expression of the TCR.

24. The isolated nucleic acid molecule of claim 23, wherein the TCR further comprises a cytoplasmic domain, wherein the cytoplasmic domain allows intracellular signaling in response to interactions between the TCR and the HIV epitope.

25. The isolated nucleic acid molecule of claim 1, wherein the mutation further increases the activity of the TCR to detect cells presenting an HIV epitope compared to the wild type TCR.

26. The isolated nucleic acid molecule of claim 1, wherein the mutation further increases the cytotoxic functional activity of the TCR against cells presenting an HIV epitope compared to the wild type TCR.

* * * * *

SEQUENCE LISTING

<160> NUMBER OF SEQ ID NOS: 44

<210> SEQ ID NO 1
<211> LENGTH: 9
<212> TYPE: PRT
<213> ORGANISM: Human immunodeficiency virus

<400> SEQUENCE: 1

Ala Ile Ile Arg Ile Leu Gln Gln Leu
1               5

<210> SEQ ID NO 2
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 2

Tyr Gln Thr Gly Ala
1               5

<210> SEQ ID NO 3
<211> LENGTH: 381
<212> TYPE: PRT
<213> ORGANISM: Unknown
<220> FEATURE:
<223> OTHER INFORMATION: Description of Unknown: AL9scTCR wild type
      protein sequence

<400> SEQUENCE: 3

Gly Glu Asp Val Glu Gln Ser Leu Phe Leu Ser Val Arg Gly Asp
1               5                   10                  15

Ser Ser Val Ile Asn Cys Thr Tyr Thr Asp Ser Ser Thr Tyr Leu
                20                  25                  30

Tyr Trp Tyr Lys Gln Glu Ser Gly Ala Gly Leu Gln Leu Leu Thr Tyr
                35                  40                  45

Ile Phe Ser Asn Met Asp Met Lys Gln Asp Gln Arg Leu Thr Val Leu
50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Glu Thr Tyr Gln Thr Gly
                85                  90                  95

Ala Asn Asn Leu Phe Phe Gly Thr Gly Thr Arg Leu Thr Val Ile Pro
                100                 105                 110

Thr Ser Gly Gly Gly Gly Ser Gly Gly Gly Ala Ser Gly Gly Gly Gly
                115                 120                 125

Ser Gly Gly Gly Gly Ser Ser Ser Glu Ala Gly Val Thr Gln Phe Pro
130                 135                 140

Ser His Ser Val Ile Glu Lys Gly Gln Thr Val Thr Leu Arg Cys Asp
145                 150                 155                 160

Pro Ile Ser Gly His Asp Asn Leu Tyr Trp Tyr Arg Arg Val Met Gly
                165                 170                 175

Lys Glu Ile Lys Phe Leu Leu His Phe Val Lys Glu Ser Lys Gln Asp
                180                 185                 190

Glu Ser Gly Met Pro Asn Asn Arg Phe Leu Ala Glu Arg Thr Gly Gly
                195                 200                 205

Thr Tyr Ser Thr Leu Lys Val Gln Pro Ala Glu Leu Glu Asp Ser Gly
                210                 215                 220

Val Tyr Phe Cys Ala Ser Ser Gln Gly Val Thr Leu Leu Asn Glu Gln
225                 230                 235                 240

Phe Phe Gly Pro Gly Thr Arg Leu Thr Val Leu Glu Asp Leu Asn Lys
                245                 250                 255

Val Phe Pro Pro Glu Val Ala Val Phe Glu Pro Ser Glu Ala Glu Ile
                260                 265                 270

Ser His Thr Gln Lys Ala Thr Leu Val Cys Leu Ala Thr Gly Phe Phe
                275                 280                 285

Pro Asp His Val Glu Leu Ser Trp Trp Val Asn Gly Lys Glu Val His
                290                 295                 300

Ser Gly Val Ser Thr Asp Pro Gln Pro Leu Lys Glu Gln Pro Ala Leu
305                 310                 315                 320

```
Asn Asp Ser Arg Tyr Cys Leu Ser Ser Arg Leu Arg Val Ser Ala Thr
                325                 330                 335

Phe Trp Gln Asn Pro Arg Asn His Phe Arg Cys Gln Val Gln Phe Tyr
            340                 345                 350

Gly Leu Ser Glu Asn Asp Glu Trp Thr Gln Asp Arg Ala Lys Pro Val
        355                 360                 365

Thr Gln Ile Val Ser Ala Glu Ala Trp Gly Arg Ala Asp
    370                 375                 380

<210> SEQ ID NO 4
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Ser Gly Ala Gly Leu Gln Leu Leu Thr Tyr
            35                  40                  45

Ile Phe Ser Asn Met Asp Met Lys Gln Asp Gln Arg Leu Thr Val Leu
    50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Glu Thr His Gln Thr Gly
                85                  90                  95

Ala Asn Asn Leu Phe Phe Gly Thr Gly Thr Arg Leu Thr Val Ile Pro
            100                 105                 110

Thr Ser Gly Gly Gly Gly Ser Gly Gly Gly Ala Ser Gly Gly Gly Gly
            115                 120                 125

Ser Gly Gly Gly Gly Ser Ser Glu Ala Gly Val Thr Gln Phe Pro
130                 135                 140

Ser His Ser Val Ile Glu Lys Gly Gln Thr Val Thr Leu Arg Cys Asp
145                 150                 155                 160

Pro Ile Ser Gly His Asp Asn Leu Tyr Trp Tyr Arg Arg Val Met Gly
                165                 170                 175

Lys Glu Ile Lys Phe Leu Leu His Phe Val Lys Glu Ser Lys Gln Asp
            180                 185                 190

Glu Ser Gly Met Pro Asn Asn Arg Phe Leu Ala Glu Arg Thr Gly Gly
        195                 200                 205

Thr Tyr Ser Thr Leu Lys Val Gln Pro Ala Glu Leu Glu Asp Ser Gly
    210                 215                 220

Val Tyr Phe Cys Ala Ser Ser Gln Gly Val Thr Leu Leu Asn Glu Gln
225                 230                 235                 240

Phe Phe Gly Pro Gly Thr Arg Leu Thr Val Leu Glu Asp Leu Asn Lys
                245                 250                 255

Val Phe Pro Pro Glu Val Ala Val Phe Glu Pro Ser Glu Ala Glu Ile
            260                 265                 270

Ser His Thr Gln Lys Ala Thr Leu Val Cys Leu Ala Thr Gly Phe Phe
        275                 280                 285

Pro Asp His Val Glu Leu Ser Trp Trp Val Asn Gly Lys Glu Val His
    290                 295                 300
```

Ser Gly Val Ser Thr Asp Pro Gln Pro Leu Lys Glu Gln Pro Ala Leu
305                 310                 315                 320

Asn Asp Ser Arg Tyr Cys Leu Ser Ser Arg Leu Arg Val Ser Ala Thr
            325                 330                 335

Phe Trp Gln Asn Pro Arg Asn His Phe Arg Cys Gln Val Gln Phe Tyr
        340                 345                 350

Gly Leu Ser Glu Asn Asp Glu Trp Thr Gln Asp Arg Ala Lys Pro Val
            355                 360                 365

Thr Gln Ile Val Ser Ala Glu Ala Trp Gly Arg Ala Asp
        370                 375                 380

<210> SEQ ID NO 5
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
        35                  40                  45

Ile Phe Ser Asn Met Asp Met Lys Gln Asp Gln Arg Leu Thr Val Leu
50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Glu Thr His Gln Thr Gly
                85                  90                  95

Ala Asn Asn Leu Phe Phe Gly Thr Gly Thr Arg Leu Thr Val Ile Pro
            100                 105                 110

Thr Ser Gly Gly Gly Gly Ser Gly Gly Gly Ala Ser Gly Gly Gly Gly
        115                 120                 125

Ser Gly Gly Gly Gly Ser Ser Glu Ala Gly Val Thr Gln Phe Pro
130                 135                 140

Ser His Ser Val Ile Glu Lys Gly Gln Thr Val Thr Leu Arg Cys Asp
145                 150                 155                 160

Pro Ile Ser Gly His Asp Asn Leu Tyr Trp Tyr Arg Arg Val Met Gly
                165                 170                 175

Lys Glu Ile Lys Phe Leu Leu His Phe Val Lys Glu Ser Lys Gln Asp
            180                 185                 190

Glu Ser Gly Met Pro Asn Asn Arg Phe Leu Ala Glu Arg Thr Gly Gly
        195                 200                 205

Thr Tyr Ser Thr Leu Lys Val Gln Pro Ala Glu Leu Glu Asp Ser Gly
    210                 215                 220

Val Tyr Phe Cys Ala Ser Ser Gln Gly Val Thr Leu Leu Asn Glu Gln
225                 230                 235                 240

Phe Phe Gly Pro Gly Thr Arg Leu Thr Val Leu Glu Asp Leu Asn Lys
                245                 250                 255

Val Phe Pro Pro Glu Val Ala Val Phe Glu Pro Ser Glu Ala Glu Ile
            260                 265                 270

Ser His Thr Gln Lys Ala Thr Leu Val Cys Leu Ala Thr Gly Phe Phe

```
              275                 280                 285
Pro Asp His Val Glu Leu Ser Trp Trp Val Asn Gly Lys Glu Val His
            290                 295                 300

Ser Gly Val Ser Thr Asp Pro Gln Pro Leu Lys Glu Gln Pro Ala Leu
305                 310                 315                 320

Asn Asp Ser Arg Tyr Cys Leu Ser Ser Arg Leu Arg Val Ser Ala Thr
                325                 330                 335

Phe Trp Gln Asn Pro Arg Asn His Phe Arg Cys Gln Val Gln Phe Tyr
            340                 345                 350

Gly Leu Ser Glu Asn Asp Glu Trp Thr Gln Asp Arg Ala Lys Pro Val
            355                 360                 365

Thr Gln Ile Val Ser Ala Glu Ala Trp Gly Arg Ala Asp
            370                 375                 380

<210> SEQ ID NO 6
<211> LENGTH: 1143
<212> TYPE: DNA
<213> ORGANISM: Unknown
<220> FEATURE:
<223> OTHER INFORMATION: Description of Unknown: AL9scTCR wild type
      nucleic acid sequence

<400> SEQUENCE: 6
ggagaggatg tggagcagag tctttttcctg agtgtccgag agggagacag ctccgttata      60
aactgcactt acacagacag ctcctccacc tactatact  ggtataagca agaatctgga     120
gcaggtctcc agttgctgac gtatattttc tcaaatatgg acatgaaaca agaccaaaga     180
ctcactgttc tattgaataa aaaggataaa catctgtctc tgcgcattgc agacacccag     240
actggggact cagctatcta cttctgtgca gagacttatc aaactggggc aaacaacctc     300
ttctttggga ctggaacgag actcaccgtt attcccacta gtggagggg  tggaagcggg     360 ggtggtgcta gcggtggcgg cggttctggc ggtggcggtt cctcaagcga agctggagtt     420
actcagttcc ccagccacag cgtaatagag aagggccaga ctgtgactct gagatgtgac     480
ccaatttctg acatgataa  tctttattgg tatcgacgtg ttatgggaaa agaaataaaa     540
tttctgttac atttttgtgaa agagtctaaa caggatgagt ccggtatgcc caacaatcga     600
ttcttagctg aaaggactgg agggacgtat tctactctga aggtgcagcc tgcagaactg     660
gaggattctg gagtttattt ctgtgccagc agccaagggg tgactttgtt gaatgagcag     720
ttcttcgggc cagggacacg gctcaccgtg ctagaggacc tgaacaaggt gttcccaccc     780
gaggtcgctg tgtttgagcc atcagaagca gagatctccc acacccaaaa ggccacactg     840
gtgtgcctgg ccacaggctt cttccctgac acgtggagc  tgagctggtg ggtgaatggg     900
aaggaggtgc acagtgggt  cagcacggac ccgcagcccc tcaaggagca gcccgccctc     960
aatgactcca gatactgcct gagcagccgc ctgagggtct cggccacctt ctggcagaac    1020
ccccgcaacc acttccgctg tcaagtccag ttctacgggc tctcggagaa tgacgagtgg    1080
acccaggata gggccaaacc cgtcacccag atcgtcagcg ccgaggcctg ggtagagca     1140 gac                                                                  1143

<210> SEQ ID NO 7
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 7

```
ggagaggatg tggagcagag tcttttcctg agtgtccgag agggagacag ctccgttata    60
aactgcactt acacagacag ctcctccacc tacttatact ggtataagca agaatctgga   120
gcaggtctcc agttgctgac gtatattttc tcaaatatgg acatgaaaca agaccaaaga   180
ctcactgttc tattgaataa aaaggataaa catctgtctc tgcgcattgc agacacccag   240
actggggact cagctatcta cttctgtgca gagactcatc aaactggggc aaacaacctc   300
ttctttggga ctggaacgag actcaccgtt attcccacta gtggaggggg tggaagcggg   360
ggtggtgcta gcggtggcgg cggttctggc ggtggcggtt cctcaagcga agctggagtt   420
actcagttcc ccagccacag cgtaatagag aagggccaga ctgtgactct gagatgtgac   480
ccaatttctg acatgataa tctttattgg tatcgacgtg ttatgggaaa agaaataaaa   540
tttctgttac attttgtgaa agagtctaaa caggatgagt ccggtatgcc caacaatcga   600
ttcttagctg aaaggactgg agggacgtat tctactctga aggtgcagcc tgcagaactg   660
gaggattctg gagtttattt ctgtgccagc agccaagggg tgactttgtt gaatgagcag   720
ttcttcgggc cagggacacg gctcaccgtg ctagaggacc tgaacaaggt gttcccaccc   780
gaggtcgctg tgtttgagcc atcagaagca gagatctccc acccaaaa ggccacactg    840
gtgtgcctgg ccacaggctt cttccctgac acgtggagc tgagctggtg ggtgaatggg    900
aaggaggtgc acagtggggt cagcacggac ccgcagcccc tcaaggagca gcccgccctc   960
aatgactcca gatactgcct gagcagccgc ctgagggtct cggccacctt ctggcagaac  1020
ccccgcaacc acttccgctg tcaagtccag ttctacgggc tctcggagaa tgacgagtgg  1080
acccaggata gggccaaacc cgtcacccag atcgtcagcg ccgaggcctg ggtagagca   1140
gac                                                                1143
```

<210> SEQ ID NO 8
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
ggagaggatg tggagcagag tcttttcctg agtgtccgag agggagacag ctccgttata    60
aactgcactt acacagacag ctcctccacc tacttatact ggtataagca agaaccggga   120
gcaggtctcc agttgctgac gtatattttc tcaaatatgg acatgaaaca agaccaaaga   180
ctcactgttc tattgaataa aaaggataaa catctgtctc tgcgcattgc agacacccag   240
actggggact cagctatcta cttctgtgca gagactcatc aaactggggc aaacaacctc   300
ttctttggga ctggaacgag actcaccgtt attcccacta gtggaggggg tggaagcggg   360
ggtggtgcta gcggtggcgg cggttctggc ggtggcggtt cctcaagcga agctggagtt   420
actcagttcc ccagccacag cgtaatagag aagggccaga ctgtgactct gagatgtgac   480
ccaatttctg acatgataa tctttattgg tatcgacgtg ttatgggaaa agaaataaaa   540
tttctgttac attttgtgaa agagtctaaa caggatgagt ccggtatgcc caacaatcga   600
ttcttagctg aaaggactgg agggacgtat tctactctga aggtgcagcc tgcagaactg   660
gaggattctg gagtttattt ctgtgccagc agccaagggg tgactttgtt gaatgagcag   720
ttcttcgggc cagggacacg gctcaccgtg ctagaggacc tgaacaaggt gttcccaccc   780
```

```
gaggtcgctg tgtttgagcc atcagaagca gagatctccc acacccaaaa ggccacactg    840
gtgtgcctgg ccacaggctt cttccctgac cacgtggagc tgagctggtg ggtgaatggg    900
aaggaggtgc acagtggggt cagcacggac ccgcagcccc tcaaggagca gcccgccctc    960
aatgactcca gatactgcct gagcagccgc ctgagggtct cggccacctt ctggcagaac   1020
ccccgcaacc acttccgctg tcaagtccag ttctacgggc tctcggagaa tgacgagtgg   1080
acccaggata gggccaaacc cgtcacccag atcgtcagcg ccgaggcctg gggtagagca   1140
gac                                                                 1143
```

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Glu Thr Asp Thr Leu Leu Leu Trp Val Leu Leu Leu Trp Val Pro
1               5                   10                  15

Gly Ser Thr Gly
            20

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Leu Asn Asp Ile Phe Glu Ala Gln Lys Ile Glu Trp His Glu
1               5                   10                  15

<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile

```
                    115                 120                 125

Ile Ser Thr Leu Thr
            130

<210> SEQ ID NO 12
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 13
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 14
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 15
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

```
Lys Ala Glu Thr Ile Pro Val Leu His Glu Met Ile Gln Gln Ile Phe
         50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Thr Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Gly Gly Gly Gly Ser Gly Gly Ala Ser Gly Gly Gly
 1               5                  10                  15

Ser Gly Gly Gly Gly Ser Ser Ser
                20

<210> SEQ ID NO 18
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Ser Gly Gly Gly Gly Ser Gly
1               5                   10                  15

Gly Gly Gly Ser
            20

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Asn Ala Lys Thr Thr Ala Pro Ser Val Tyr Pro Leu Ala Pro Val
1               5                   10                  15

Ser

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atggagacag acacactcct gttatgggta ctgctgctct gggttccagg ttccaccggt      60

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtggtctga acgacatctt cgaagctcag aaaattgaat ggcacgaa                    48

<210> SEQ ID NO 22
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gcacctactt caagttctac aaagaaaaca cagctacaac tggagcattt actgctggat      60
ttacagatga ttttgaatgg aattaataat acaagaatc ccaaactcac caggatgctc     120
acatttaagt tttacatgcc caagaaggcc acagaactga acatcttca gtgtctagaa     180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
```
tggattacct tttgtcaaag catcatctca acactaact                                399

<210> SEQ ID NO 23
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga    360
ccgtcagtct tcctcttccc cccaaaaccc aaggacaccc tcatgatctc ccggaccccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990

<210> SEQ ID NO 24
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
aactgggtga atgtaataag tgatttgaaa aaaattgaag atcttattca atctatgcat      60
attgatgcta ctttatatac ggaaagtgat gttcacccca gttgcaaagt aacagcaatg     120
aagtgctttc tcttggagtt acaagttatt tcacttgagt ccggagatgc aagtattcat     180
gatacagtag aaaatctgat catcctagca acaacagttt gtcttctaa tgggaatgta     240
acagaatctg gatgcaaaga atgtgaggaa ctggaggaaa aaatattaa agaattttttg     300
cagagttttg tacatattgt ccaaatgttc atcaacactt ct                        342

<210> SEQ ID NO 25
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atcacgtgcc ctcccccat gtccgtggaa cacgcagaca tctgggtcaa gagctacagc      60
ttgtactcca gggagcggta catttgtaac tctggtttca agcgtaaagc cggcacgtcc     120
agcctgacgg agtgcgtgtt gaacaaggcc acgaatgtcg cccactggac aacccccagt    180
ctcaaatgca ttaga                                                     195
```

<210> SEQ ID NO 26
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
tgtgatctgc ctcaaaccca cagcctgggt agcaggagga ccttgatgct cctggcacag     60
atgaggagaa tctctctttt ctcctgcttg aaggacagac atgactttgg atttccccag    120
gaggagtttg gcaaccagtt ccaaaaggct gaaaccatcc ctgtcctcca tgagatgatc    180
cagcagatct tcaatctctt cagcacaaag gactcatctg ctgcttggga tgagaccctc    240
ctagacaaat tctacactga actctaccag cagctgaatg acctggaagc ctgtgtgata    300
caggggtgg gggtgacaga gactcccctg atgaaggagg actccattct ggctgtgagg    360
aaatacttcc aaagaatcac tctctatctg aagagaaga aatacagccc ttgtgcctgg    420
gaggttgtca gagcagaaat catgagatct ttttctttgt caacaaactt gcaagaaagt    480
ttaagaagta aggaa                                                    495
```

<210> SEQ ID NO 27
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gcacccgccc gctcgcccag ccccagcacg cagccctggg agcatgtgaa tgccatccag     60
gaggcccggc gtctcctgaa cctgagtaga gacactgctg ctgagatgaa tgaaacagta    120
gaagtcatct cagaaatgtt tgacctccag gagccgacct gcctacagac ccgcctggag    180
ctgtacaagc agggcctgcg gggcagcctc accaagctca agggccccctt gaccatgatg    240
gccagccact acaagcagca ctgccctcca accccggaaa cttcctgtgc aacccagact    300
atcacctttg aaagtttcaa agagaacctg aaggactttc tgcttgtcat cccctttgac    360
tgctgggagc cagtccagga g                                              381
```

<210> SEQ ID NO 28
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

```
actagtggag ggggtggaag cgggggtggt gctagcggtg gcggcggttc tggcggtggc     60
ggttcctcaa gc                                                        72
```

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtggcggtg gcagcggcgg tggtggttcc ggtggcggcg gttctggcgg tggcggttcc         60

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gttaacgcaa agacaaccgc cccttcagta tatccactag cgcccgtt                      48

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ile Ile Arg Ile Ala Gln Gln Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ala Ile Arg Ile Leu Gln Gln Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ile Ile Arg Ile Leu Ala Gln Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Ala Ile Ile Ala Ile Leu Gln Gln Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ile Ile Arg Ile Leu Gln Ala Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ile Ile Arg Ile Leu Gln Gln Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Leu Ile Arg Ile Leu Gln Gln Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ile Ile Arg Met Leu Gln Gln Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ile Ile Arg Thr Leu Gln Gln Leu
1               5

<210> SEQ ID NO 40
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 40

Ala Ile Thr Arg Ile Leu Gln Gln Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ile Met Arg Ile Leu Gln Gln Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ile Ile Asp Ile Leu Gln Gln Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ile Ile Lys Ile Leu Gln Gln Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Ile Ile Arg Met Ala Gln Gln Leu
1               5
```